United States Patent
Harding et al.

(10) Patent No.: US 7,294,369 B2
(45) Date of Patent: Nov. 13, 2007

(54) POLYMERISABLE CINNAMATES WITH LATERAL SUBSTITUTION

(75) Inventors: Richard Harding, Eastleigh (GB); Ian Victor Edward Hassall, Christchurch (GB); Shirley Ann Marden, Parkstone (GB); Darren Brown, Parkstone (GB)

(73) Assignee: Merck Patent Gesellschaft Mit Beschrankter Haftung, Darmstadt (DE)

( * ) Notice: Subject to any disclaimer, the term of this patent is extended or adjusted under 35 U.S.C. 154(b) by 270 days.

(21) Appl. No.: 10/965,851

(22) Filed: Oct. 18, 2004

(65) Prior Publication Data

US 2005/0227021 A1    Oct. 13, 2005

(30) Foreign Application Priority Data

Oct. 17, 2003    (EP)    ................... 03023430

(51) Int. Cl.
| | |
|---|---|
| *C09K 19/38* | (2006.01) |
| *C09K 19/52* | (2006.01) |
| *C09K 19/34* | (2006.01) |
| *C09K 19/32* | (2006.01) |
| *C09K 19/20* | (2006.01) |
| *C07C 69/78* | (2006.01) |

(52) U.S. Cl. ............. 428/1.1; 252/299.61; 252/299.62; 252/299.67; 560/8

(58) Field of Classification Search ................. 428/1.1; 252/299.01, 299.61, 299.62, 299.67; 560/8
See application file for complete search history.

(56) References Cited

U.S. PATENT DOCUMENTS 5,770,107 A    6/1998    Hassall et al.

2004/0142116 A1    7/2004    Ohkawa et al.
2006/0193998 A1*    8/2006    Harding et al. ............. 428/1.1
2006/0193999 A1*    8/2006    Verall et al. ................. 428/1.1

FOREIGN PATENT DOCUMENTS

GB    2388600    11/2003

OTHER PUBLICATIONS

Yaroshchuk O et al., "Liquid-crystal photalignment using low-molecular-weight photo-cross-linkable composites," Applied Physics Letters, Jul. 2, 2001, vol. 79, No. 1, pp. 30-32, XP012028755, ISSN: 0003-6951, the whole document, American Institute of Physics, New York, US.

Tejedor R M et al., "Synthesis and Characterization of Two Isomeric Liquid Crystal Series With Reactive Double Bonds," Liquid Crystals, Taylor and Francis LTD, London, GB, Nov. 1, 1993, pp. 689-700, vol. 15, No. 5, XP000414620, ISSN: 0267-8292.

* cited by examiner

*Primary Examiner*—Shean C. Wu
(74) *Attorney, Agent, or Firm*—Millen, White, Zelano & Branigan, P.C.

(57) ABSTRACT

The invention relates to new polymerisable mesogenic or liquid crystalline compounds comprising a laterally substituted cinnamate group, to polymerisable mesogenic or liquid crystalline mixtures and anisotropic polymers prepared thereof, and to the use of the new compounds and the mixtures and polymers prepared thereof in optical and electrooptical devices, adhesives, synthetic resins with anisotropic mechanical properties, cosmetics, diagnostics, liquid crystal pigments, decorative and security applications, nonlinear optics, optical information storage, electronic devices like organic field effect transistors (FET or OFET), electroluminescent devices, or as chiral dopants.

20 Claims, No Drawings

POLYMERISABLE CINNAMATES WITH LATERAL SUBSTITUTION

FIELD OF THE INVENTION

The invention relates to new polymerisable mesogenic or liquid crystalline compounds comprising a laterally substituted cinnamate group, to polymerisable mesogenic or liquid crystalline mixtures and anisotropic polymers prepared thereof, and to the use of the new compounds and the mixtures and polymers prepared thereof in optical and electrooptical devices, adhesives, synthetic resins with anisotropic mechanical properties, cosmetics, diagnostics, liquid crystal pigments, decorative and security applications, nonlinear optics, optical information storage, electronic devices like organic field effect transistors (FET or OFET), electroluminescent devices, or as chiral dopants.

BACKGROUND AND PRIOR ART

Polymerisable mesogenic or liquid crystal (LC) compounds, which are also known as reactive mesogens (RM), have been described in prior art for various purposes. For example, they can be used for the preparation of linear or crosslinked liquid crystal side chain polymers. Furthermore, they can be aligned in their liquid crystal phase and subsequently polymerized in situ to give linear or crosslinked liquid crystal polymer films with uniform orientation of high quality. These films can be used as optical elements like polarisers or compensators in flat panel displays, as described for example in EP 0 397 263, WO 98/00475, WO 98/04651 or WO 98/12584.

RMs have also been suggested for use in polymerised cholesteric liquid crystal films or coatings that show selective reflection of visible light and are suitable as optical films like narrowband or broadband reflective polarizers or colour filters as described for example in EP 0 606 940 or WO 97/35219, or for the preparation of liquid crystal pigments, as described for example in WO 97/30136. Other important fields of use are security markings as described for example in U.S. Pat. No. 5,678,863 or hot stamping foils as described for example in GB 2,357,061.

Furthermore, isomerisable RMs are known in prior art which show E-Z or cis-trans isomerisation upon photoirradiation and are thereby change their shape and physical properties like the birefringence or, in case of chiral compounds, their chirality and twisting power. Such photoisomerisable RMs have been suggested for example for the preparation of cholesteric polymer films with patterned optical properties, which can be used as optical components like colour filters or broadband reflective polarizers in liquid crystal displays. The preparation of patterned cholesteric films is described for example in WO 00/34808. Also, they can be used as photoorientable materials for applications using photoalignment by irradiation with linear polarized light, like the preparation of alignment layers or optical films having a pattern of regions with different orientation, as described for example in U.S. Pat. No. 5,602,661. Furthermore, photoisomerisable RMs have been suggested for use in cholesteric or multi-domain liquid crystal displays, as disclosed in WO 98/57223.

It is known that RMs comprising a cinnamic acid group are suitable as photoisomerisable or photoorientable materials. Such compounds are described for example in U.S. Pat. No. 5,770,107.

However, the compounds of prior art are often difficult to synthesise. The intermediate cinnamic acids show only limited solubility in organic solvents which is disadvantageous for synthesis. For example, the prior art materials cannot be reacted under standard Dean and Stark conditions because the material is insoluble in dichloromethane DCM. This creates problems because quantities of THF has to be added in order to aid solubility of the intermediate cinnamic acid to allow reaction to occur. This process is far from optimal, because even in THF the intermediate is only partially soluble. For example 20 volumes THF can be used to recrystallise the cinnamic acid intermediate. In contrast the new, laterally siubstituted cinnamic acids (used to synthesise materials of Formula I) are soluble in DCM, enabling them to be reacted using standard Dean & Stark conditions.

Therefore, there is a demand for photoisomerisable or photo-orientable RMs which are easy to synthesize in a large range of derivatives, show good solubility in DCM, have a low melting point, do not negatively affect the liquid crystal phase behaviour of LC mixtures or polymerisable LC mixtures and are suitable for the uses as mentioned above. The materials should preferably posses a broad liquid crystal phases, in particular a nematic phase, and be highly miscible with other reactive liquid crystal materials. In this way they can posses suitable values of the birefringence Δn ranging preferably from 0 to 0.4.

The invention has the aim of providing photoisomerisable and photoorientable polymerisable mesogenic or liquid crystal compounds having these properties, but not having the disadvantages of the compounds of prior art as discussed above. Another aim of the invention is to extend the pool of reactive photoisomerisable compounds available to the expert.

The inventors of the present invention have found that these aims can be achieved by providing compounds as claimed in the present invention.

Definitions of Terms

The term 'film' as used in this application includes self-supporting, i.e. free-standing, films that show more or less pronounced mechanical stability and flexibility, as well as coatings or layers on a supporting substrate or between two substrates.

The term 'mesogenic compounds' as used in the foregoing and the following should denote compounds with a rod-shaped, lath-shaped or disk-shaped mesogenic group, i.e. a group with the ability to induce mesophase behaviour. These compounds do not necessarily have to exhibit mesophase behaviour by themselves. It is also possible that these compounds show mesophase behaviour only in mixtures with other compounds or when the mesogenic compounds or the mixtures comprising them are polymerized. Rod-shaped and lath-shaped mesogenic groups are especially preferred.

For the sake of simplicity, the term 'liquid crystal (LC) material' is used hereinafter for both liquid crystal materials and mesogenic materials, and the term 'mesogen' is used for the mesogenic groups of the material.

Polymerisable compounds with one polymerisable group are also referred to as 'monoreactive' compounds, compounds with two polymerisable groups as 'direactive' compounds, and compounds with more than two polymerisable groups as 'multireactive' compounds. Compounds without a polymerisable group are also referred to as 'non-reactive' compounds.

A polymerisable mesogenic or liquid crystal compound is also shortly referred to as 'reactive mesogen (RM)'.

SUMMARY OF THE INVENTION

The present invention relates to compounds of formula I

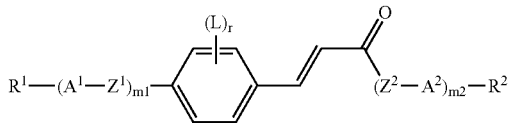

$A^1$ and $A^2$ are each independently an aliphatic or aromatic carbocyclic or heterocyclic group with up to 20 C atoms that may also comprise fused rings and may be unsubstituted, mono- or polysubstituted with L, m1 is 0, 1, 2 or 3, m2 is 1, 2, 3 or 4, $Z^1$ and $Z^2$ are independently of each other —O—, —S—, —CO—, —COO—, —OCO—, —S—CO—, —CO—S—, —O—COO—, —CO—NR$^1$—, —NR$^0$—CO—, —OCH$_2$—, —CH$_2$O—, —SCH$_2$—, —CH$_2$S—, —CF$_2$O—, —OCF$_2$—, —CF$_2$S—, —SCF$_2$—, —CH$_2$CH$_2$—, —CF$_2$CH$_2$—, —CH$_2$CF$_2$—, —CF$_2$CF$_2$—, —CH=N—, —N=CH—, —N=N—, —CH=CR$^0$—, —CY$^1$=CY$^2$—, —C≡C—, —CH=CH—COO—, —OCO—CH=CH— or a single bond, $Y^1$ and $Y^2$ are independently of each other H, F, Cl or CN, $R^0$ and $R^{00}$ are independently of each other H or alkyl with 1 to 12 C-atoms, $R^1$ and $R^2$ are independently of each other H, F, Cl, Br, I, CN, NO$_2$, NCS, SF$_5$ or straight chain or branched alkyl having 1 to 30 C-atoms that is unsubstituted, mono- or polysubstituted by F, Cl, Br, I or CN, and in which one or more non-adjacent CH$_2$ groups are optionally replaced, in each case independently from one another, by —O—, —S—, —NH—, —NR$^0$—, —SiR$^0$R$^{00}$—, —CO—, —COO—, —OCO—, —OCO—O—, —S—CO—, —CO—S—, —CY$^1$=CY$^2$— or —C≡C— in such a manner that O and/or S atoms are not linked directly to one another, or denote P-Sp, wherein at least one of $R^1$ and $R^2$ is P-Sp, P is a polymerisable group, Sp is a spacer group or a single bond, L has, in case of multiple occurrence independently of one another, one of the meanings of $R^1$ different from H, and r is 1, 2, 3 or 4.

The invention further relates to a polymerisable liquid crystal material comprising at least one compound of formula I.

The invention further relates to an anisotropic polymer or polymer film obtained from one or more compounds of formula I or from a polymerisable liquid crystal material comprising at least one compound of formula I.

The invention further relates to the use of a compound of formula I, polymerisable material or polymer prepared thereof in optical films, polarisers, compensators, biaxial films, beam splitters, reflective films, alignment layers, colour filters, holographic elements, hot stamping foils, coloured images, decorative or security markings, liquid crystal pigments, adhesives, synthetic resins with anisotropic mechanical properties, cosmetics, diagnostics, nonlinear optics, optical information storage, as chiral dopants, in electronic devices like for example field effect transistors (FET) as components of integrated circuitry, as thin film transistors in flat panel display applications or for Radio Frequency Identification (RFID) tags, or in semiconducting components for organic light emitting diode (OLED) applications such as electroluminescent displays or backlights of e.g. liquid crystal displays, for photovoltaic or sensor devices, as electrode materials in batteries, as photoconductors, or for electrophotographic applications like electrophotographic recording.

The invention further relates to a liquid crystal mixture or a polymer gel or network comprising one or more compounds of formula I and one or more low molar mass liquid crystal compounds.

The invention further relates to a display comprising in its active layer at least one compound of formula I or a liquid crystal mixture or polymer comprising at least one compound of formula I.

DETAILED DESCRIPTION OF THE INVENTION

The compounds of formula I are especially suitable for use in liquid crystalline polymerisable compositions for applications utilising photoisomersation or photoorientation. They do not have to exhibit mesophase behaviour themsleves, but can also show mesophase behaviour in mixtures with other compounds. However, compounds of formula I with broad LC phases are especially preferred.

Furthermore, the compounds of formula I are monomers with a high solubility, and are easy to synthesize in broad varieties.

Particularly preferred are compounds of formula I, wherein m1+m2=1 or 2, m1 is 0, m2 is 1 or 2, $A^1$ and $A^2$ are an aromatic group, preferably if m1 or m2 is 1, m2 is 1 and $A^1$ is optionally substituted 1,4-phenylene, $Z^1$ and $Z^2$ are selected from —COO—, —OCO—, —C≡C— and —CY$^1$=CY$^2$—, r is 1 or 2, $R^1$ or $R^2$ are selected from F, Cl, CN or alkyl, alkoxy, sulfanylalkyl, thiocarboxyl, alkylsulfonyl or alkenyl with 1 to 12 C-atoms which is optionally fluorinated, $R^1$ is P-Sp-, $R^1$ and $R^2$ are P-Sp, Sp is alkylene with 1 to 12 C atoms which is optionally mono- or polysubstituted by F and wherein one or more non-adjacent CH$_2$ may be replaced, in each case independently from one another, by —O—, —CH=CH— or —C≡C—, Sp is a single bond.

Further preferred are compounds of formula I, wherein

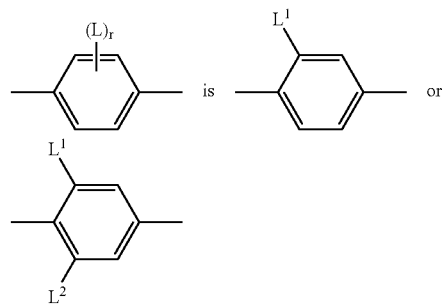

wherein L¹ and L² have independently of each other one of the meanings of L as given in formula I or as given below.

L in formula I is preferably F, Cl, Br, I, CN, NO₂ or alkyl, alkoxy, alkylcarbonyl, alkoxycarbonyl, alkylcarbonlyoxy or alkoxycarbonyloxy with 1 to 20 C atoms, wherein one or more H atoms may be substituted by F or Cl.

Especially preferred groups L are F, Cl, CN, NO₂, CH₃, C₂H₅, OCH₃, OC₂H₅, COCH₃, COC₂H₅, COOCH₃, COOC₂H₅, CF₃, OCF₃, OCHF₂ or OC₂F₅, in particular F, Cl, CN, CH₃, C₂H₅, OCH₃, COCH₃ or OCF₃, most preferably F, Cl, CH₃, OCH₃ or COCH₃.

A¹ and A² in formula I are preferably an aromatic or alicyclic 5- or 6-ring, or a group comprising two or three fused aromatic or alicyclic 5- or 6-rings, wherein these rings may also contain one or more hetero atoms, in particular selected from N, O and S, and may also be mono- or polysubstituted by L.

Preferred groups A¹ and A² in formula I are for example furan, pyrrol, thiophene, oxazole, thiazole, thiadiazole, imidazole, phenylene, pyridine, pyrimidine, pyrazine, indane, naphthalene, tetrahydronaphthalene, anthracene and phenanthrene.

Particularly preferably A¹ and A² are selected from furane-2,5-diyl, thiophene-2,5-diyl, pyrrol-2,5-diyl, 1,4-phenylene, pyridine-2,5-diyl, pyrimidine-2,5-diyl, naphthalene-2,6-diyl, 1,2,3,4-tetrahydro-naphthalene-2,6-diyl, indane-2,5-diyl, furthermore 1,4-cyclohexylene in which, in addition, one or two non-adjacent CH₂ groups may be replaced by O and/or S, wherein these groups are unsubstituted or mono- or polysubstituted by L as defined above.

Preferably the groups $(Z^1-A^1)_{m1}$ and $(A^2-Z^2)_{m2}$ in formula I contain only monocyclic groups A¹ and A². Very preferably the groups $-(A^1-Z^1)_{m1}-$ and $-(Z^2-A^2)_{m2}-$ denote independently of each other a group with one or two five- or six-membered rings. The groups $-(A^1-Z^1)_{m1}-$ and $-(Z^2-A^2)_{m2}-$ may be identical or different. Particularly preferred are compounds wherein $-(A^1-Z^1)_{m1}-$ and $-(Z^2-A^2)_{m2}-$ are different.

Preferred subformulae for the groups $-(A^1-Z^1)_{m1}-$ and $-(Z^2-A^2)_{m2}-$ are listed below. For reasons of simplicity, Phe in these groups is 1,4-phenylene, Phe L is a 1,4-phenylene group which is substituted by 1 to 4 groups L as defined above, Pyd is pyridine-2,5-diyl and Pyr is pyrimidine-2,5-diyl. The following list of preferred groups $-(A^1-Z^1)_{m1}-$ and $-(Z^2-A^2)_{m2}-$ is comprising the subformulae 11-1 to 11-16 as well as their mirror images, which are linked via the radical Z to the tolane group in formula I -Phe-Z- II-1
-Pyd-Z- II-2
-Pyr-Z- II-3
-PheL-Z- II-4
-Phe-Z-Phe-Z- II-5
-Phe-Z-Pyd-Z- II-6
-Pyd-Z-Phe-Z- II-7
-Phe-Z-Pyr-Z- II-8
-Pyr-Z-Phe-Z- II-9
-PheL-Z-Phe-Z- II-10
-PheL-Z-Pyd-Z- II-11
-PheL-Z-Pyr-Z- II-12
-Pyr-Z-Pyd-Z- II-13
-Pyd-Z-Pyd-Z- II-14
-Pyr-Z-Pyr-Z- II-15
-PheL-Z-PheL-Z- II-16

In these preferred groups Z has the meaning of Z¹ as given in formula I. Preferably Z is —COO—, —OCO—, —CH₂CH₂—C≡C— or a single bond.

Very preferably $-(A^1-Z^1)_{m1}-$ and $-(Z^2-A^2)_{m2}-$ are, independently of each other, selected from the following formulae and their mirror images, which are linked via the radical Z to the tolane group in formula I

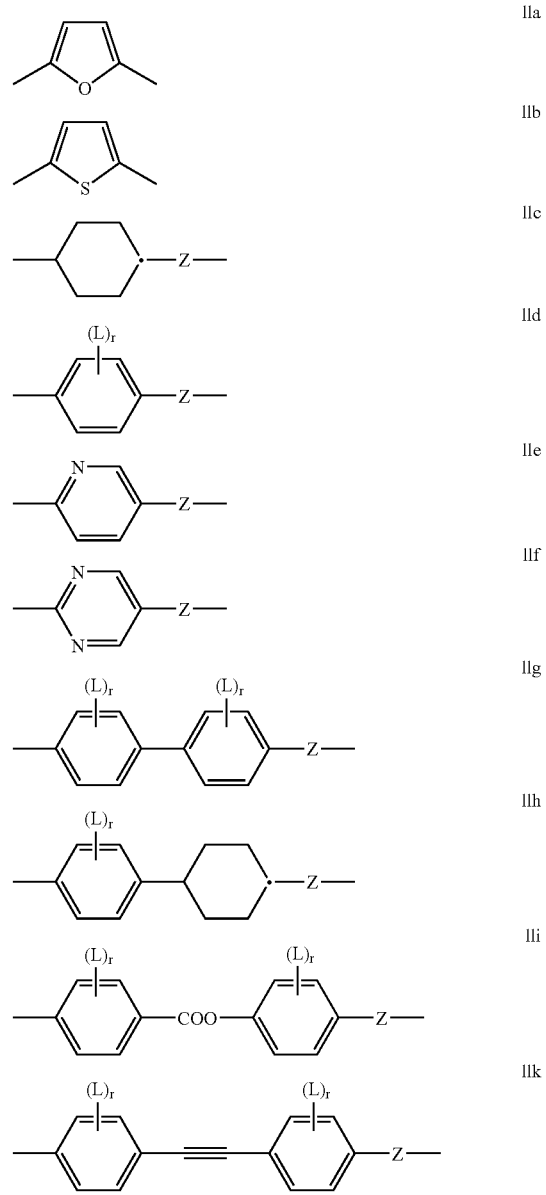

wherein Z and L have the meaning given above and r is 0, 1, 2, 3 or 4, preferably 0, 1 or 2.

For the group $-(A^1-Z^1)_{m1}-$ attached to the acetylene group in formula I, Z in the preferred formulae IIa to IIf is preferably a single bond.

The group

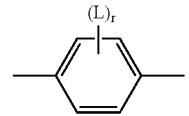

in these preferred formulae is very preferably denoting

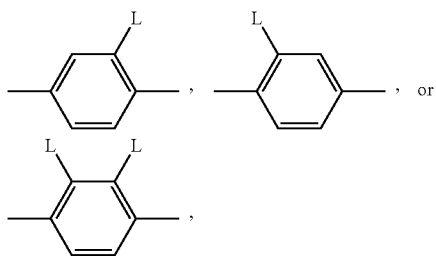

furthermore

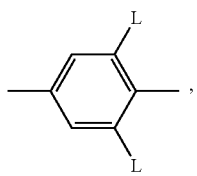

with L having each independently one of the meanings given above.

Particularly preferred are the subformulae IIa, IIc, IIf, IIg and IIh, in particular the subformulae IIa, IId and IIf.

Especially preferred are compounds of formula I comprising at least one group

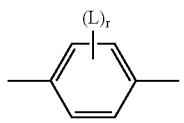

wherein r is 1.

Further preferred are compounds of formula I comprising at least two groups

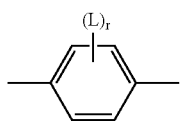

wherein r is 1 and/or at least one group

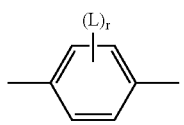

wherein r is 2.

In another preferred embodiment one or more of $A^1$ and $A^2$ are a bivalent chiral group, or together with $R^1$ or $R^2$ in formula I form a terminal chiral group.

Preferred chiral groups $A^{1/2}$ and $A^{1/2}$-$R^{1/2}$ are for example cholesteryl, terpenoid radicals as disclosed e.g. in WO 96/17901, preferably selected from menthyl, neomenthyl, campheyl, pineyl, terpineyl, isolongifolyl, fenchyl, carreyl, myrthenyl, nopyl, geraniyl, linaloyl, neryl, citronellyl and dihydrocitronellyl, in particular menthyl or menthone derivatives or terminal chiral sugar derivatives comprising a mono- or bicyclic radical with pyranose or furanose rings like, for example, a group derived from the chiral sugars disclosed in WO 95/16007.

Preferred chiral groups $A^{1/2}$ and $A^{1/2}$-$R^{1/2}$ are for example cholesteryl or groups derived from sugars, binaphthyl derivatives, or optically active glycols, especially ethane-1, 2-diol substituted in 1- and or 2-position with alkyl or aryl groups. In case of sugar groups, these are preferably selected from mono- and dicyclic groups comprising pentose or hexose rings.

Particularly preferred are the following groups $A^{1/2}$ and $A^{1/2}$-$R^{1/2}$

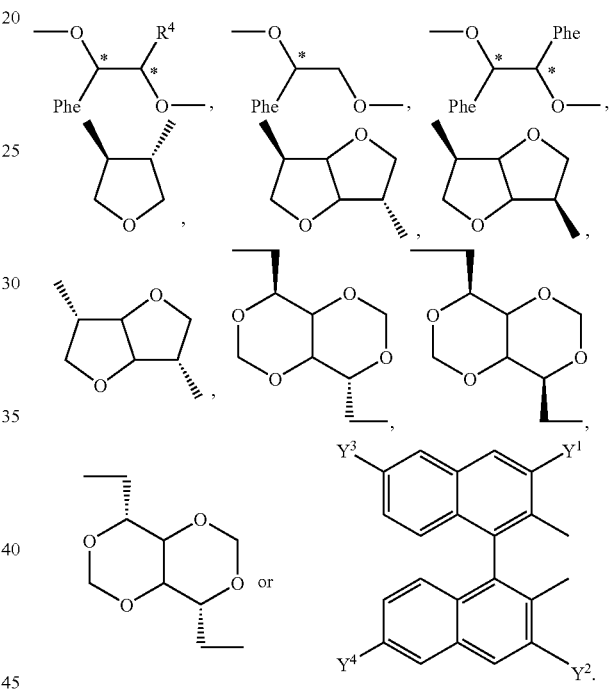

wherein Phe has the meaning given above, $R^4$ is F or optionally fluorinated alkyl with 1 to 4 C atoms and $Y^1$, $Y^2$, $Y^3$ and $Y^4$ have one of the meanings of $R^1$ in formula I.

Preferably $A^{1/2}$ or $A^{1/2}$-$R^{1/2}$ is dianhydrosorbitol, substituted ethane diol like

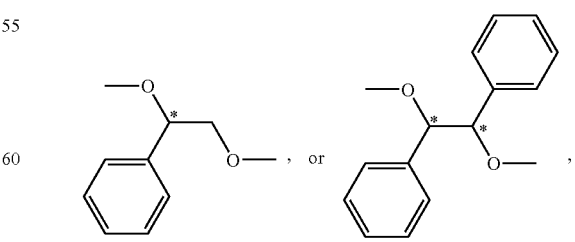

wherein $R^4$ is F, $CH_3$ or $CF_3$, or optionally substituted binaphthyl

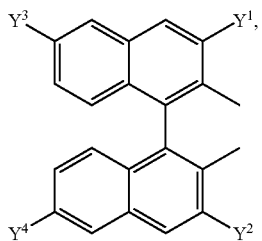

wherein $Y^1$, $Y^2$, $Y^3$ and $Y^4$ are H, F or optionally fluorinated alkyl with 1 to 8 C atoms.

$CY^1=CY^2$ is preferably —CH=CH—, —CH=CF—, —CF=CH—, —CF=CF—, —CH=C(CN)— or —C(CN)=CH—.

If $R^1$ or $R^2$ in formula I is an alkyl or alkoxy radical, i.e. where the terminal CH$_2$ group is replaced by —O—, this may be straight-chain or branched. It is preferably straight-chain, has 2, 3, 4, 5, 6, 7 or 8 carbon atoms and accordingly is preferably ethyl, propyl, butyl, pentyl, hexyl, heptyl, octyl, ethoxy, propoxy, butoxy, pentoxy, hexoxy, heptoxy, or octoxy, furthermore methyl, nonyl, decyl, undecyl, dodecyl, tridecyl, tetradecyl, pentadecyl, nonoxy, decoxy, undecoxy, dodecoxy, tridecoxy or tetradecoxy, for example.

Oxaalkyl, i.e. where one CH$_2$ group is replaced by —O—, is preferably straight-chain 2-oxapropyl (=methoxymethyl), 2- (=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-, 7-, 8- or 9-oxadecyl, for example.

If $R^1$ or $R^2$ is an alkylsulfanyl radical, i.e. alkyl where the CH$_2$ group that is linked to the adjacent group is replaced by —S—, this may be straight chain or branched. It is preferably straight chain, has 1, 2, 3, 4, 5, 6, 7 or 8 carbon atoms and accordingly is preferably methylsulfanyl, ethylsulfanyl, propylsulfanyl, butylsulfanyl, pentylsulfanyl, hexylsulfanyl, heptylsulfanyl, octylsulfanyl, furthermore nonylsulfanyl, decylsulfanyl, undecylsulfanyl or dodecylsulfanyl, for example.

If $R^1$ or $R^2$ is a thiocarboxyl or alkylsulfanylcarbonyl group, i.e. alkyl wherein the CH$_2$ group that is linked to the neighboured group is replaced by —CO—S— or —S—CO—, this may be straight chain or branched. It is preferably straight chain, has 2, 3, 4, 5, 6, 7 or 8 carbon atoms and accordingly is preferably thioacetyl, thiopropionyl, thiobutyryl, thiopentanoyl, thiohexanoyl, thioheptanoyl, thiooctanoyl, methylsulfanylcarbonyl, ethylsulfanylcarbonyl, propylsulfanylcarbonyl, butylsulfanylcarbonyl, pentylsulfanylcarbonyl, hexylsulfanylcarbonyl or heptylsulfanylcarbonyl, for example.

If $R^1$ or $R^2$ is an alkylsulfonyl group, i.e. alkyl wherein the CH$_2$ group that is neighboured to the adjacent group is replaced by a sulfonyl group —SO$_2$—, this may be straight chain or branched. It is preferably straight chain, has 1, 2, 3, 4, 5, 6, 7 or 8 carbon atoms and accordingly is preferably methylsulfone, ethylsulfone, propylsulfone, butylsulfone, pentylsulfone, hexylsulfone, heptylsulfone or octylsulfone, furthermore nonylsulfone, decylsulfone, undecylsulfone or dodecylsulfone, for example.

If $R^1$ or $R^2$ is an alkyl group wherein one or more CH$_2$ groups are replaced by —CH=CH—, this may be straight-chain or branched. It is preferably straight-chain, has 2 to 10 C atoms and accordingly is preferably vinyl, prop-1-, or prop-2-enyl, but-1-, 2- or but-3-enyl, pent-1-, 2-, 3- or pent-4-enyl, hex-1-, 2-, 3-, 4- or hex-5-enyl, hept-1-, 2-, 3-, 4-, 5- or hept-6-enyl, oct-1-, 2-, 3-, 4-, 5-, 6- or oct-7-enyl, non-1-, 2-, 3-, 4-, 5-, 6-, 7- or non-8-enyl, dec-1-, 2-, 3-, 4-, 5-, 6-, 7-, 8- or dec-9-enyl.

Especially preferred alkenyl groups are $C_2$-$C_{71}$ E-alkenyl, $C_4$-$C_7$-3E-alkenyl, $C_5$-$C_7$-4-alkenyl, $C_6$-$C_7$-5-alkenyl and $C_{7-6}$-alkenyl, in particular $C_2$-$C_7$-1 E-alkenyl, $C_4$-$C_7$-3E-alkenyl and $C_5$-$C_7$-4-alkenyl. Examples for particularly preferred alkenyl groups are vinyl, 1 E-propenyl, 1 E-butenyl, 1 E-pentenyl, 1 E-hexenyl, 1 E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 C atoms are generally preferred.

If $R^1$ or $R^2$ is an alkyl group, wherein one CH$_2$ group is replaced by —O— and one by —CO—, these radicals are preferably neighboured. Accordingly these radicals together form a carbonyloxy group —CO—O— or an oxycarbonyl group —O—CO—. Preferably this group is straight-chain and has 2 to 6 C atoms.

It is accordingly preferably acetyloxy, propionyloxy, butyryloxy, pentanoyloxy, hexanoyloxy, acetyloxymethyl, propionyloxymethyl, butyryloxymethyl, pentanoyloxymethyl, 2-acetyloxyethyl, 2-propionyloxyethyl, 2-butyryloxyethyl, 3-acetyloxypropyl, 3-propionyloxypropyl, 4-acetyloxybutyl, methoxycarbonyl, ethoxycarbonyl, propoxycarbonyl, butoxycarbonyl, pentoxycarbonyl, methoxycarbonylmethyl, ethoxycarbonylmethyl, prbpoxycarbonylmethyl, butoxycarbonylmethyl, 2-(methoxycarbonyl) ethyl, 2-(ethoxycarbonyl)ethyl, 2-(propoxy-carbonyl)ethyl, 3-(methoxycarbonyl)propyl, 3-(ethoxycarbonyl)propyl, 4-(methoxycarbonyl)-butyl.

If $R^1$ or $R^2$ is an alkyl group, wherein two or more CH$_2$ groups are replaced by —O— and/or —COO—, it can be straight-chain or branched. It is preferably straight-chain and has 3 to 12 C atoms. Accordingly it is preferably bis-carboxy-methyl, 2,2-bis-carboxy-ethyl, 3,3-bis-carboxy-propyl, 4,4-bis-carboxy-butyl, 5,5-bis-carboxy-pentyl, 6,6-bis-carboxy-hexyl, 7,7-bis-carboxy-heptyl, 8,8-bis-carboxy-octyl, 9,9-bis-carboxy-nonyl, 10,10-bis-carboxy-decyl, bis-(methoxycarbonyl)-methyl, 2,2-bis-(methoxycarbonyl)-ethyl, 3,3-bis-(methoxycarbonyl)-propyl, 4,4-bis-(methoxycarbonyl)-butyl, 5,5-bis-(methoxycarbonyl)-pentyl, 6,6-bis-(methoxycarbonyl)-hexyl, 7,7-bis-(methoxycarbonyl)-heptyl, 8,8-bis-(methoxycarbonyl)-octyl, bis-(ethoxycarbonyl)-methyl, 2,2-bis-(ethoxycarbonyl)-ethyl, 3,3-bis-(ethoxycarbonyl)-propyl, 4,4-bis-(ethoxycarbonyl)-butyl, 5,5-bis-(ethoxycarbonyl)-hexyl.

If $R^1$ or $R^2$ is an alkyl or alkenyl group that is monosubstituted by CN or CF$_3$, it is preferably straight-chain. The substitution by CN or CF$_3$ can be in any desired position.

If $R^1$ or $R^2$ is an alkyl or alkenyl group that is at least monosubstituted by halogen, it is preferably straight-chain. Halogen is preferably F or Cl, in case of multiple substitution preferably F. The resulting groups include also perfluorinated groups. In case of monosubstitution the F or Cl substituent can be in any desired position, but is preferably in ω-position. Examples for especially preferred straight-chain groups with a terminal F substituent are fluormethyl, 2-fluorethyl, 3-fluorpropyl, 4-fluorbutyl, 5-fluorpentyl, 6-fluorhexyl and 7-fluorheptyl. Other positions of F are, however, not excluded.

Halogen is preferably F or Cl.

$R^1$ or $R^2$ in formula I can be a polar or a non-polar group. In case of a polar group, it is selected from CN, SF$_5$, halogen, OCH$_3$, SCN, COR$^5$, COOR$^5$ or a mono- oligo- or polyfluorinated alkyl or alkoxy group with 1 to 4 C atoms. $R^5$ is optionally fluorinated alkyl with 1 to 4, preferably 1 to 3 C atoms. Especially preferred polar groups are selected of F, Cl, CN, $OCH_3$, $COCH_3$, $COC_2H_5$, $COOCH_3$, $COOC_2H_5$, $CF_3$, $CHF_2$, $CH_2F$, $OCF_3$, $OCHF_2$, $OCH_2F$, $C_2F_5$ and $OC_2F_5$, in particular F, Cl, CN, $CF_3$, $OCHF_2$ and $OCF_3$. In case of a non-polar group, it is preferably alkyl with up to 15 C atoms or alkoxy with 2 to 15 C atoms.

$R^1$ or $R^2$ in formula I can be an achiral or a chiral group. In case of a chiral group it is preferably selected of formula III:

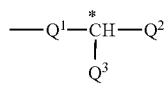

wherein $Q^1$ is an alkylene or alkylene-oxy group with 1 to 9 C atoms or a single bond, $Q^2$ is an alkyl or alkoxy group with 1 to 10 C atoms which may be unsubstituted, mono- or polysubstituted by F, Cl, Br or CN, it being also possible for one or more non-adjacent $CH_2$ groups to be replaced, in each case independently from one another, by —C≡C—, —O—, —S—, —NH—, —N($CH_3$)—, —CO—, —COO—, —OCO—, —OCO—O—, —S—CO— or —CO—S— in such a manner that oxygen atoms are not linked directly to one another, $Q^3$ is F, Cl, Br, CN or an alkyl or alkoxy group as defined for $Q^2$ but being different from $Q^2$.

In case $Q^1$ in formula III is an alkylene-oxy group, the O atom is preferably adjacent to the chiral C atom.

Preferred chiral groups of formula III are 2-alkyl, 2-alkoxy, 2-methylalkyl, 2-methylalkoxy, 2-fluoroalkyl, 2-fluoroalkoxy, 2-(2-ethin)-alkyl, 2-(2-ethin)-alkoxy, 1,1,1-trifluoro-2-alkyl and 1,1,1-trifluoro-2-alkoxy.

Particularly preferred chiral groups are 2-butyl (=1-methylpropyl), 2-methylbutyl, 2-methylpentyl, 3-methylpentyl, 2-ethylhexyl, 2-propylpentyl, in particular 2-methylbutyl, 2-methylbutoxy, 2-methylpentoxy, 3-methylpentoxy, 2-ethylhexoxy, 1-methylhexoxy, 2-octyloxy, 2-oxa-3-methylbutyl, 3-oxa-4-methylpentyl, 4-methylhexyl, 2-hexyl, 2-octyl, 2-nonyl, 2-decyl, 2-dodecyl, 6-methoxyoctoxy, 6-methyloctoxy, 6-methyloctanoyloxy, 5-methylheptyloxycarbonyl, 2-methylbutyryloxy, 3-methylvaleroyloxy, 4-methylhexanoyloxy, 2-chlorpropionyloxy, 2-chloro-3-methylbutyryloxy, 2-chloro-4-methylvaleryloxy, 2-chloro-3-methylvaleryloxy, 2-methyl-3-oxapentyl, 2-methyl-3-oxahexyl, 1-methoxypropyl-2-oxy, 1-ethoxypropyl-2-oxy, 1-propoxypropyl-2-oxy, 1-butoxypropyl-2-oxy, 2-fluorooctyloxy, 2-fluorodecyloxy, 1,1,1-trifluoro-2-octyloxy, 1,1,1-trifluoro-2-octyl, 2-fluoromethyloctyloxy for example. Very preferred are 2-hexyl, 2-octyl, 2-octyloxy, 1,1,1-trifluoro-2-hexyl, 1,1,1-trifluoro-2-octyl and 1,1,1-trifluoro-2-octyloxy.

In addition, compounds of formula I containing an achiral branched group $R^1$ or $R^2$ may occasionally be of importance, for example, due to a reduction in the tendency towards crystallization. Branched groups of this type generally do not contain more than one chain branch. Preferred achiral branched groups are isopropyl, isobutyl (=methylpropyl), isopentyl (=3-methylbutyl), isopropoxy, 2-methyl-propoxy and 3-methylbutoxy.

The polymerisable or reactive group P is preferably selected from $CH_2=CW^1$—COO—,

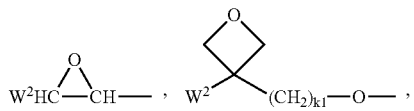

$CH_2=CW^2$—(O)$_{k1}$—, $CH_3$—CH═CH—O—, ($CH_2$═CH)$_2$CH—OCO—, ($CH_2$═CH—$CH_2$)$_2$CH—OCO—, ($CH_2$═CH)$_2$CH—O—, ($CH_2$═CH—$CH_2$)$_2$N—, HO—$CW^2W^3$—, HS—$CW^2W^3$—, $HW^2$N—, HO-$CW^2W^3$—NH—, $CH_2$═$CW^1$—CO—NH—, $CH_2$═CH—(COO)$_{k1}$-Phe-(O)$_{k2}$—, Phe-CH═CH—, HOOC—, OCN—, and $W^4W^5W^6$Si—, with $W^1$ being H, Cl, CN, phenyl or alkyl with 1 to 5 C-atoms, in particular H, Cl or $CH_3$, $W^2$ and $W^3$ being independently of each other H or alkyl with 1 to 5 C-atoms, in particular H, methyl, ethyl or n-propyl, $W^4$, $W^5$ and $W^6$ being independently of each other Cl, oxaalkyl or oxacarbonylalkyl with 1 to 5 C-atoms, Phe being 1,4-phenylene and $k_1$ and $k_2$ being independently of each other 0 or 1.

Especially preferably P is a group without a carbonyl moiety, preferably selected from

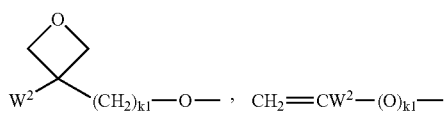

and $CH_3$—CH═CH—O— as defined above, very preferably a vinyl group $CH_2$═CH—, a vinyl ether group $CH_2$═CH—O—, a propenyl ether group $CH_3$—CH═CH—O— or an oxetane group of formula

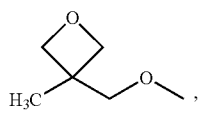

most preferably a vinyl ether group.

As for the spacer group Sp all groups can be used that are known for this purpose to the skilled in the art. The spacer group Sp is preferably of formula Sp'-X, such that P-Sp- is P-Sp'-X-, wherein Sp' is alkylene with up to 30 C atoms which is unsubstituted or mono- or polysubstituted by F, Cl, Br, I or CN, it being also possible for one or more non-adjacent $CH_2$ groups to be replaced, in each case independently from one another, by —O—, —S—, —NH—, —$NR^0$—, —$SiR^0R^{00}$—, —CO—, —COO—, —OCO—, —OCO—O—, —S—CO—, —CO—S—, —CH═CH— or —C≡C— in such a manner that O and/or S atoms are not linked directly to one another, X is —O—, —S—, —CO—, —COO—, —OCO—, —O—COO—, —CO—$NR^0$—, —$NR^0$—CO—, —$OCH_2$—, —$CH_2O$—, —$SCH_2$—, —$CH_2S$—, —$CF_2O$—, —$OCF_2$—, —$CF_2S$—, —$SCF_2$—, —$CF_2CH_2$—, —$CH_2CF_2$—, —$CF_2CF_2$—, —CH═N—, —N═CH—, —N═N—, —CH═$CR^0$—, —$CY^1$═$CY^2$—, —C≡C—, —CH═CH—COO—, —OCO—CH═CH— or a single bond, and $R^0$, $R^{00}$, $Y^1$ and $Y^2$ have one of the meanings given above.

X is preferably —O—, —S—, —OCH$_2$—, —CH$_2$O—, —SCH$_2$—, —CH$_2$S—, —CF$_2$O—OCF$_2$—, —CF$_2$S—, —SCF$_2$—, —CH$_2$CH$_2$—, —CF$_2$CH$_2$—, —CH$_2$CF$_2$—, —CF$_2$CF$_2$—, —CH=N—, —N=CH—, —N=N—, —CH=CR$^0$—, —CX$^1$=CX$^2$—, —C≡C— or a single bond, in particular —O—, —S—, —C≡C—, —CX$^1$=CX$^2$— or a single bond. In another preferred embodiment X is a group that is able to form a conjugated system, such as —C≡C— or —CX$^1$=CX$^2$—, or a single bond.

Typical groups Sp' are, for example, —(CH$_2$)$_p$—, —(CH$_2$CH$_2$O)$_q$-CH$_2$CH$_2$—, —CH$_2$CH$_2$—S—CH$_2$CH$_2$— or —CH$_2$CH$_2$—NH—CH$_2$CH$_2$— or —(SiR$^0$R$^{00}$-O)$_p$—, with p being an integer from 2 to 12, q being an integer from 1 to 3 and R$^0$ and R$^{00}$ having the meanings given above.

Preferred groups Sp' are ethylene, propylene, butylene, pentylene, hexylene, heptylene, octylene, nonylene, decylene, undecylene, dodecylene, octadecylene, ethyleneoxyethylene, methyleneoxybutylene, ethylene-thioethylene, ethylene-N-methyl-iminoethylene, 1-methylalkylene, ethenylene, propenylene and butenylene for example.

In another preferred embodiment Sp' is a chiral group of formula IV:

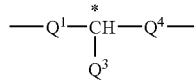

IV wherein

Q$^1$ and Q$^3$ have the meanings given in formula III, and

Q$^4$ is an alkylene or alkylene-oxy group with 1 to 10 C atoms or a single bond, being different from Q$^1$, with Q$^1$ being linked to the polymerizable group P.

Further preferred are compounds with one or two groups P-Sp-wherein Sp is a single bond.

In case of compounds with two groups P-Sp, each of the two polymerisable groups P and the two spacer groups Sp can be identical or different.

Particularly preferred compounds of formula I are those of the following formula

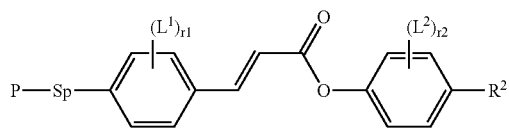

I1 wherein P, Sp and R$^2$ have the meanings of formula I, L$^1$ and L$^2$ have independently of each other one of the meanings of L given above, r1 is 1, 2, 3 or 4 and r2 is 0, 1, 2, 3 or 4.

Particularly preferred are compounds of the above formulae wherein R$^2$ is P-Sp-X, furthermore those, wherein R$^2$ is F, Cl, CN, or optionally fluorinated alkyl or alkoxy with 1 to 8 C-atoms. Further preferred are compounds wherein r1 is 1 or 2 and r2 is 0, 1 or 2.

Especially preferred compounds of formula I1 are the following

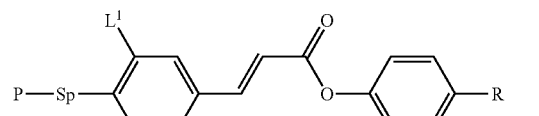

I1a

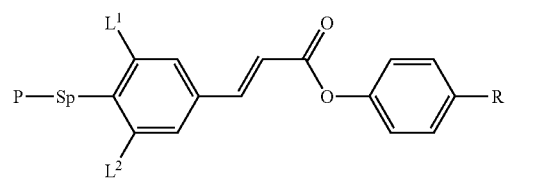

I1b

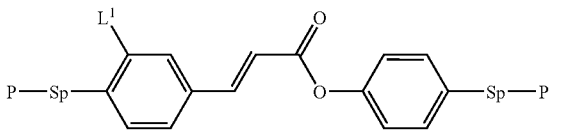

I1c

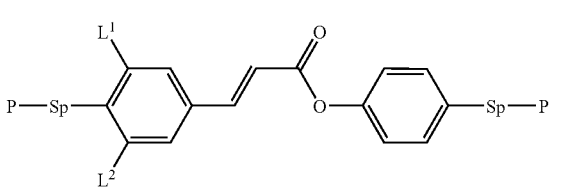

I1d wherein R has one of the meanings of R$^2$ different from P-Sp, and is preferably Cl, CN or alkyl or alkoxy with 1 to 8 C-atoms, P-Sp have the manings given above, and L$^1$ and L$^2$ have the meanings given above, and are preferably F, Cl, CN, CH$_3$, C$_2$H$_5$, OCH$_3$, COCH$_3$, OC$_2$H$_5$ or OCF$_3$.

The compounds of formula I can be synthesized according to or in analogy to methods which are known per se and which are described in standard works of organic chemistry such as, for example, Houben-Weyl, Methoden der organischen Chemie, Thieme-Verlag, Stuttgart. Some specific methods of preparation can be taken from the examples.

The compounds of formula I and polymerisable liquid crystal mixtures comprising them are useful for the preparation of anisotropic polymer films or coatings.

For the preparation of anisotropic polymer films, the liquid crystal mixture according to the present invention should comprise at least one polymerisable compound, which can be a compound of formula I or an additional polymerisable mesogenic or liquid crystalline compound.

In a preferred embodiment of the present invention the polymerisable material comprises at least one di- or multireactive achiral polymerisable mesogenic compound and at least one monoreactive achiral polymerisable mesogenic compound.

In another preferred embodiment of the present invention the polymerisable material comprises at least one two monoreactive achiral polymerisable mesogenic compounds.

In a preferred embodiment of the present invention the polymerisable material comprises at least one di- or multireactive chiral polymerisable mesogenic compound and at least one mono-, di- or multireactive achiral polymerisable mesogenic compound.

In another preferred embodiment of the present invention the polymerisable material comprises at least one monoreactive chiral polymerisable mesogenic compound and at least one mono-, di- or multireactive achiral polymerisable mesogenic compound.

In another preferred embodiment the polymerisable material comprises at least one non-reactive chiral compound and at least one mono-, di- or multireactive polymerisable mesogenic compound.

If di- or multireactive compounds are present in the polymerisable material, a three-dimensional polymer network is formed. An optical retardation film made of such a network is self-supporting and shows a high mechanical and thermal stability and a low temperature dependence of its physical and optical properties.

By varying the concentration of the di- and multireactive compounds the crosslink density of the polymer film and thereby its physical and chemical properties such as the glass transition temperature, which is also important for the temperature dependence of the optical properties of the optical retardation film, the thermal and mechanical stability or the solvent resistance can be tuned easily.

A preferred polymerisable LC mixture comprises
5 to 100% of one or more compounds of formula I,
0-80%, preferably 5 to 50% of one or more direactive achiral mesogenic compounds,
5-80%, preferably 5 to 70% of one or more monoreactive achiral mesogenic compounds,
0-80%, preferably 5 to 50% of one or more mono- or direactive chiral mesogenic compounds and/or 0-20% of one or more non-reactive chiral compounds which may also be mesogenic,
0 to 15%, preferably 0.1 to 10%, very preferably 0.5 to 5% of one or more photoinitiators, preferably at least one of which is a liquid crystal photoinitiator,
0 to 10% of one or more chain transfer agents,
0 to 3% of one or more non-reactive, monoreactive, di- or multireactive surfactants.

Polymerisable mesogenic mono-, di- and multireactive compounds used for the present invention can be prepared by methods which are known per se and which are described, for example, in standard works of organic chemistry such as, for example, Houben-Weyl, Methoden der organischen Chemie, Thieme-Verlag, Stuttgart.

Examples of suitable polymerizable mesogenic compounds that can be used as monomers or comonomers in a polymerizable LC mixture according to the present invention are disclosed for example in WO 93/22397, EP 0 261 712, DE 195 04 224, WO 95/22586, WO 97/00600 and GB 2 351 734. The compounds disclosed in these documents, however, are to be regarded merely as examples that shall not limit the scope of this invention.

Examples of especially useful chiral and achiral polymerizable mesogenic compounds (reactive mesogens) are shown in the following lists which should, however, be taken only as illustrative and is in no way intended to restrict, but instead to explain the present invention:

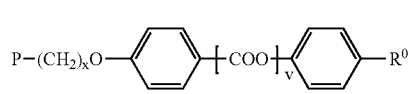 (R1)

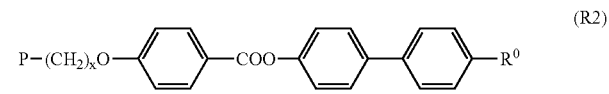 (R2)

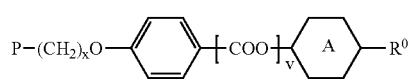 (R3)

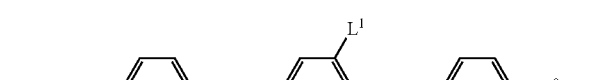 (R4)

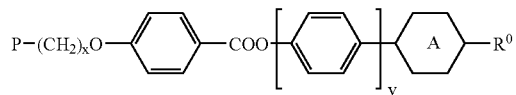 (R5)

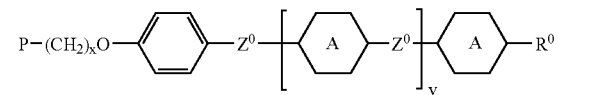 (R6)

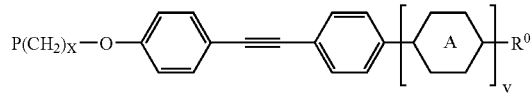 (R7)

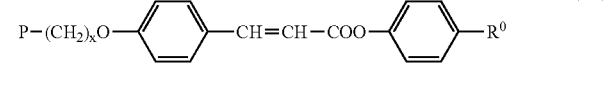 (R8)

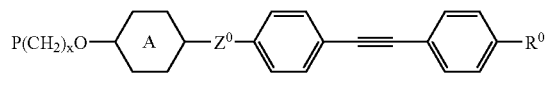 (R9)

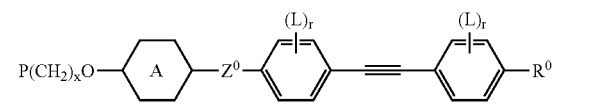 (R10)

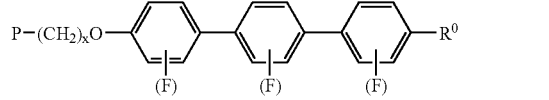 (R11)

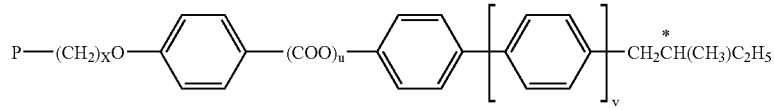 (R12)

-continued
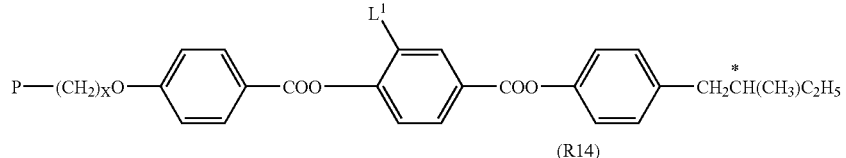 (R13)
(R14) (R15)
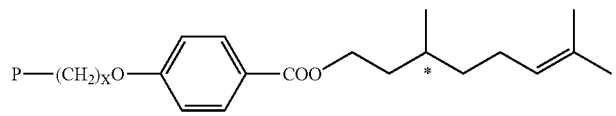 (R16)
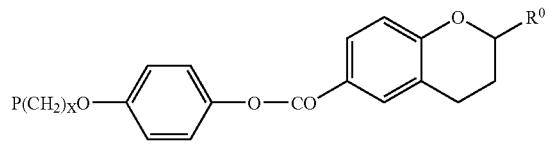 (R17)
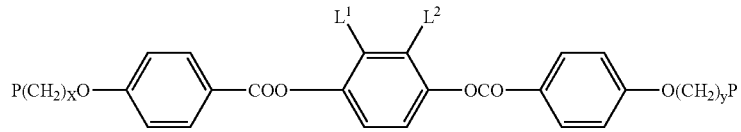 (R18)
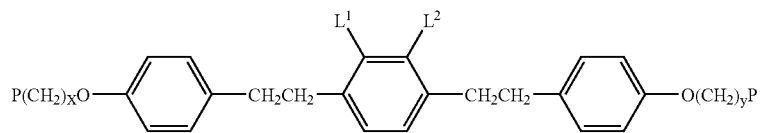 (R19)
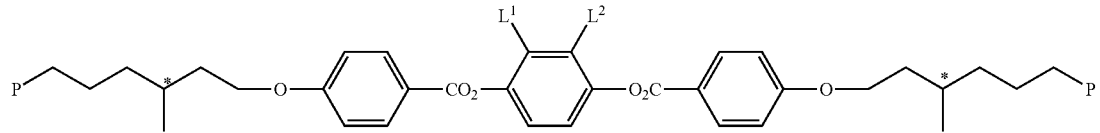 (R20)
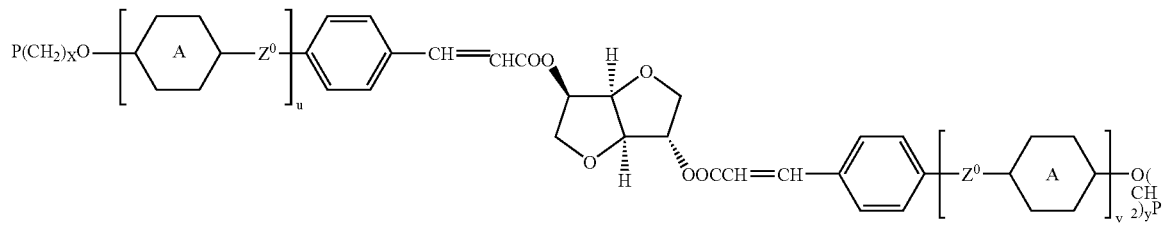 (R21)
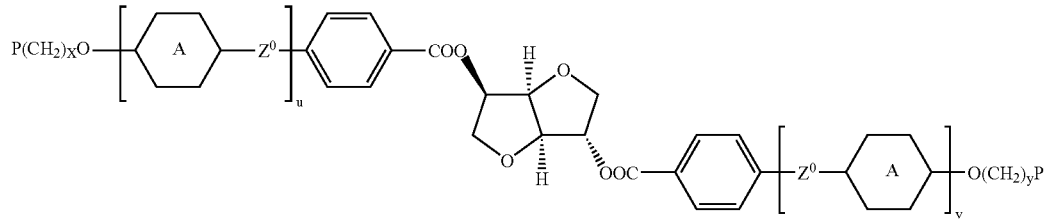 (R22)

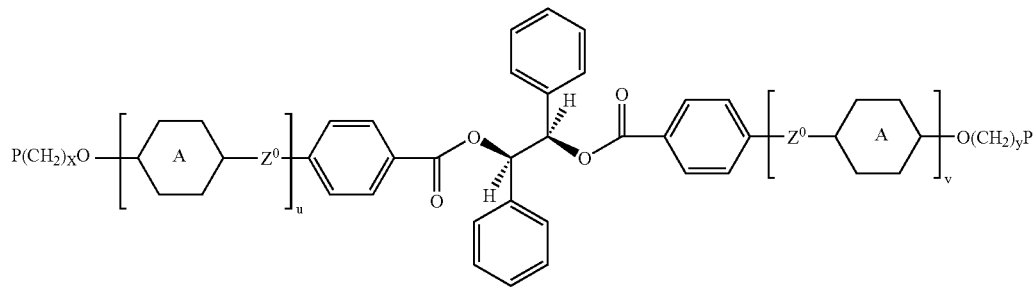
(R23)

In the above formulae, P is a polymerisable group, preferably an acryl, methacryl, vinyl, vinyloxy, propenyl ether, epoxy, oxetane or styryl group, x and y are identical or different integers from 1 to 12, A is 1,4-phenylene that is optionally mono-, di- or trisubstituted by $L^1$, or 1,4-cyclohexylene, u and v are independently of each other 0 or 1, $Z^0$ is —COO—, —OCO—, —CH$_2$CH$_2$—, —CH=CH—, —C≡C— or a single bond, $R^0$ is a polar group or an unpolar group, Ter is a terpenoid radical like e.g. menthyl, Chol is a cholesteryl group, L, $L^1$ and $L^2$ are independently of each other H, F, Cl, CN or an optionally halogenated alkyl, alkoxy, alkylcarbonyl, alkylcarbonyloxy, alkoxycarbonyl or alkoxycarbonyloxy group with 1 to 7 C atoms, and r is 0, 1, 2, 3 or 4. The phenyl rings in the above formulae are optionally substituted by 1, 2, 3 or 4 groups L.

The term 'polar group' in this connection means a group selected from F, Cl, CN, NO$_2$, OH, OCH$_3$, OCN, SCN, an optionally fluorinated alkycarbonyl, alkoxycarbonyl, alkylcarbonyloxy or alkoxycarbonyloxy group with up to 4 C atoms or a mono- oligo- or polyfluorinated alkyl or alkoxy group with 1 to 4 C atoms. The term 'unpolar group' means an optionally halogenated alkyl, alkoxy, alkycarbonyl, alkoxycarbonyl, alkylcarbonyloxy or alkoxycarbonyloxy group with 1 or more, preferably 1 to 12 C atoms which is not covered by the above definition of 'polar group'.

Suitable chiral dopants can be selected e.g. from the commercially available R- or S-811, R- or S-1011, R- or S-2011, R- or S-3011, R- or S-4011, R- or S-5011, or CB 15 (from Merck KGaA, Darmstadt, Germany). Very preferred are chiral compounds with a high helical twisting power (HTP), in particular compounds comprising a sorbitol group as described in WO 98/00428, compounds comprising a hydrobenzoin group as described in GB 2,328,207, chiral binaphthyl derivatives as described in WO 02/94805, chiral binaphthol acetal derivatives as described in WO 02/34739, chiral TADDOL derivatives as described in WO 02/06265, and chiral compounds having at least one fluorinated linkage group and a terminal or central chiral group as described in WO 02/06196 and WO 02/06195.

The photoradiation used to cause photoisomerisation of the compounds of formula I is preferably UV-radiation with a wavelength in the UV-A range (320-400 nm) or with a wavelength of 365 nm.

For preparation of a polymer film, the polymerisable LC material is preferably coated onto substrate, aligned into a uniform orientation and polymerised to permanently fix the cholesteric structure. As a substrate for example a glass or quarz sheet or a plastic film or sheet can be used. It is also possible to put a second substrate on top of the coated mixture prior to and/or during and/or after polymerisation.

The substrates can be removed after polymerisation or not. When using two substrates in case of curing by actinic radiation, at least one substrate has to be transmissive for the actinic radiation used for the polymerisation. Isotropic or birefringent substrates can be used. In case the substrate is not removed from the polymerized film after polymerisation, preferably isotropic substrates are used.

Preferably at least one substrate is a plastic substrate such as for example a film of polyester such as polyethyleneterephthalate (PET) or polyethylenenaphthalate (PEN), of polyvinylalcohol (PVA), polycarbonate (PC) or triacetylcellulose (TAC), especially preferably a PET film or a TAC film. As a birefringent substrate for example an uniaxially stretched plastic film can be used. For example PET films are commercially available from DuPont Teijin Films under the trade name Melinex®.

The polymerisable material can also be dissolved in a solvent, preferably in an organic solvent. The solution is then coated onto the substrate, for example by spin-coating or other known techniques, and the solvent is evaporated off before polymerization. In most cases it is suitable to heat the mixture in order to facilitate the evaporation of the solvent.

Polymerisation of the LC material is preferably achieved by exposing it to heat or actinic radiation. Actinic radiation means irradiation with light, like UV light, IR light or visible light, irradiation with X-rays or gamma rays or irradiation with high energy particles, such as ions or electrons. Preferably polymerisation is carried out by photoirradiation, in particular with UV light, very preferably with linear polarised UV light. As a source for actinic radiation for example a single UV lamp or a set of UV lamps can be used. When using a high lamp power the curing time can be reduced. Another possible source for photoradiation is a laser, like e.g. a UV laser, an IR laser or a visible laser.

Polymerisation is preferably carried out in the presence of an initiator absorbing at the wavelength of the actinic radiation. For example, when polymerising by means of UV light, a photoinitiator can be used that decomposes under UV irradiation to produce free radicals or ions that start the polymerisation reaction. UV photoinitiators are preferred, in particular radicalic UV photoinitiators.

Preferably the polymerisable mixture comprises one or more conventional or liquid crystal photoinitators. As standard photoinitiator for radical polymerisation for example the commercially available Irgacure® 651, Irgacure® 184, Darocure® 1173 or Darocure® 4205 (all from Ciba Geigy AG) can be used, whereas in case of cationic photopolymerisation the commercially available UVI 6974 (Union Carbide) can be used. As LC photoinitiator for example one of the compounds disclosed in EP-A-1388538 or the following compound can be used:

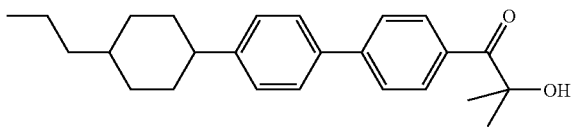

The curing time is dependent, inter alia, on the reactivity of the polymerisable material, the thickness of the coated layer, the type of polymerisation initiator and the power of the UV lamp. The curing time according to the invention is preferably not longer than 10 minutes, particularly preferably not longer than 5 minutes and very particularly preferably shorter than 2 minutes. For mass production short curing times of 3 minutes or less, very preferably of 1 minute or less, in particular of 30 seconds or less, are preferred.

The polymerisable LC material can additionally comprise one or more other suitable components such as, for example, catalysts, sensitizers, stabilizers, chain-transfer agents, inhibitors, accelerators, co-reacting monomers, surface-active compounds, lubricating agents, wetting agents, dispersing agents, hydrophobing agents, adhesive agents, flow improvers, defoaming agents, deaerators, diluents, reactive diluents, auxiliaries, colourants, dyes or pigments.

The mixture may also comprise one or more dyes having an absorption maximum adjusted to the wavelength of the radiation used for polymerisation, in particular UV dyes like e.g. 4,4'-azoxy anisole or the commercially available Tinuvin (from Ciba AG, Basel, Switzerland).

In another preferred embodiment the mixture of polymerisable material comprises up to 70%, preferably 1 to 50% of one or more non-mesogenic compounds with one polymerisable functional group. Typical examples are alkylacrylates or alkylmethacrylates.

It is also possible, in order to increase crosslinking of the polymers, to add up to 20% of one or more non-mesogenic compounds with two or more polymerisable functional groups to the polymerisable LC material alternatively or in addition to the di- or multireactive polymerisable mesogenic compounds to increase crosslinking of the polymer. Typical examples for direactive non-mesogenic monomers are alkyldiacrylates or alkyldimethacrylates with alkyl groups of 1 to 20 C atoms. Typical examples for multireactive non-mesogenic monomers are trimethylpropanetrimethacrylate or pentaerythritoltetraacrylate.

It is also possible to add one or more chain transfer agents to the polymerisable material in order to modify the physical properties of the inventive polymer film. Especially preferred are thiol compounds, such as monofunctional thiol compounds like e.g. dodecane thiol or multifunctional thiol compounds like e.g. trimethylpropane tri(3-mercaptopropionate), very preferably mesogenic or liquid crystalline thiol compounds as for example disclosed in WO 96/12209, WO 96/25470 or U.S. Pat. No. 6,420,001. When adding a chain transfer agent, the length of the free polymer chains and/or the length of the polymer chains between two crosslinks in the inventive polymer film can be controlled. When the amount of the chain transfer agent is increased, the polymer chain length in the obtained polymer film is decreasing.

When preparing a polymer film, it is usually necessary to achieve uniform alignment of the polymerisable material. For example, some uses require planar alignment, i.e. wherein in case of an achiral material the LC director is oriented parallel to the film plane, or in case of a cholesteric material the cholesteric helix axis is oriented substantially perpendicular to the film plane. Planar alignment can be achieved for example by shearing the material, e.g. by means of a doctor blade. It is also possible to apply an alignment layer, for example a layer of rubbed polyimide or sputtered $SiO_x$, on top of at least one of the substrates. Planar alignment can also be achieved by rubbing the substrate without applying an additional alignment layer, e.g. by means of a rubbing cloth or a rubbing roller. Planar alignment with a low tilt angle can also be achieved by adding one or more surfactants to the polymerizable mesogenic material. Suitable surfactants are described for example in J. Cognard, Mol.Cryst.Liq.Cryst. 78, Supplement 1, 1-77 (1981). Particularly preferred are non-ionic surfactants, e.g. non-ionic fluorocarbon surfactants, like the commercially available Fluorad® (from 3M), or Zonyl FSN® (from DuPont), or polymerizable surfactants as disclosed in EP 1 256 617 A1. Further preferred are multiblock surfactants as disclosed in GB 2 383 040 A.

In some cases it is of advantage to apply a second substrate to aid alignment and exclude oxygen that may inhibit the polymerisation. Alternatively the curing can be carried out under an atmosphere of inert gas. However, curing in air is also possible using suitable photoinitiators and high UV lamp power. When using a cationic photoinitiator oxygen exclusion most often is not needed, but water should be excluded. In a preferred embodiment of the invention the polymerisation of the polymerisable material is carried out under an atmosphere of inert gas, preferably under a nitrogen atmosphere.

Furthermore, the compounds of formula I are suitable as comonomers for liquid crystal materials with semiconductor or charge carrier properties, which can be used in electronic devices like for example field effect transistors (FET) as components of integrated circuitry, as thin film transistors in flat panel display applications or for Radio Frequency Identification (RFID) tags, or semiconducting components for organic light emitting diode (OLED) applications such as electroluminescent displays or backlights of e.g. liquid crystal displays, photovoltaic or sensor devices, photoconductors, or electrophotographic applications like electrophotographic recording devices.

For example, semiconductors comprising polymerisable liquid crystal compounds are disclosed in WO 00/79617, JP-A-2000-347432, JP-A-11-209761, Sirringhaus et al., Appl. Phys. Lett., 77(3) (2000) 406408, and Grell et al., J. Korean Phys. Soc. 2000, 36(6), 331. Electroluminescent devices using liquid crystal materials are described for example in WO 95/17018 and WO 95/04306. Organic photoconductors with liquid crystal properties are described for example in EP 0 563 768 and EP 0 527 376.

Another object of the invention is a liquid crystal mixture, in particular a nematic liquid crystal mixture, comprising at least one compound of formula I.

Yet another object of the invention is a liquid crystal display comprising a liquid crystal medium containing at least one compound of formula I.

For the applications described above the liquid crystal mixture preferably contains at least one compound of formula I, and a nematic host mixture comprising one or more nematic or nematogenic compounds.

Preferably the liquid crystal mixture consists of 2 to 25, preferably 3 to 15 compounds, at least one of which is a compound of formula I. The other compounds, forming the nematic host mixture, are preferably low molecular weight liquid crystal compounds selected from nematic or nematogenic substances, for example from the known classes of the azoxybenzenes, benzylidene-anilines, biphenyls, terphenyls, phenyl or cyclohexyl benzoates, phenyl or cyclohexyl esters of cyclohehexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid and of cyclo-hexylcyclohexanecarboxylic acid, phenylcyclohexanes, cyclohexyl-biphenyls, phenylcyclohexylcyclohexanes, cyclohexylcyclohexanes, cyclohexylcyclohexenes, cyclohexylcyclohexylcyclohexenes, 1,4-bis-cyclohexylbenzenes, 4,4'-bis-cyclohexylbiphenyls, phenyl- or cyclo-hexylpyrimidines, phenyl- or cyclohexylpyridines, phenyl- or cyclo-hexylpyridazines, phenyl- or cyclohexyldioxanes, phenyl- or cyclo-hexyl-1,3-dithianes, 1,2-diphenyl-ethanes, 1,2-dicyclohexylethanes, 1-phenyl-2-cyclohexylethanes, 1-cyclohexyl-2-(4-phenylcyclohexyl)-ethanes, 1-cyclohexyl-2-biphenyl-ethanes, 1-phenyl2-cyclohexyl-phenylethanes, optionally halogenated stilbenes, benzyl phenyl ether, tolanes, substituted cinnamic acids and further classes of nematic or nematogenic substances. The 1,4-phenylene groups in these compounds may also be laterally mono- or difluorinated.

The liquid crystal mixture of this preferred embodiment is based on the achiral compounds of this type.

The most important compounds that are possible as components of these liquid crystal mixtures can be characterized by the following formula

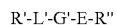

wherein L' and E, which may be identical or different, are in each case, independently from one another, a bivalent radical from the group formed by -Phe-, -Cyc-, -Phe-Phe-, -Phe-Cyc-, -Cyc-Cyc-, -Pyr-, -Dio-, -B-Phe- and -B-Cyc- and their mirror images, where Phe is unsubstituted or fluorine-substituted 1,4-phenylene, Cyc is trans-1,4-cyclohexylene or 1,4-cyclohexenylene, Pyr is pyrimidine-2,5-diyl or pyridine-2,5-diyl, Dio is 1,3-dioxane-2,5-diyl abd B is 2-(trans-1,4-cyclohexyl)ethyl, pyrimidine-2,5-diyl, pyridine-2,5-diyl or 1,3-dioxane-2,5-diyl.

G' in these compounds is selected from the following bivalent groups —CH═CH—, —N(O)N—, —CH═CY—, —CH═N(O)—, —C≡C—, —CH$_2$—CH$_2$—, —CO—O—, —CH$_2$—O—, —CO—S—, —CH$_2$—S—, —CH═N—, —COO-Phe-COO— or a single bond, with Y being halogen, preferably chlorine, or —CN.

R' and R" are, in each case, independently of one another, alkyl, alkenyl, alkoxy, alkenyloxy, alkanoyloxy, alkoxycarbonyl or alkoxycarbonyloxy with 1 to 18, preferably 3 to 12 C atoms, or alternatively one of R' and R" is F, CF$_3$, OCF$_3$, Cl, NCS or CN.

In most of these compounds R' and R" are, in each case, independently of each another, alkyl, alkenyl or alkoxy with different chain length, wherein the sum of C atoms in nematic media generally is between 2 and 9, preferably between 2 and 7.

Many of these compounds or mixtures thereof are commercially available. All of these compounds are either known or can be prepared by methods which are known per se, as described in the literature (for example in the standard works such as Houben-Weyl, Methoden der Organischen Chemie [Methods of Organic Chemistry], Georg-Thieme-Verlag, Stuttgart), to be precise under reaction conditions which are known and suitable for said reactions. Use may also be made here of variants which are known per se, but are not mentioned here.

The compounds of formula I can be used in a liquid crystal mixture for displays like, for example, TN or STN displays, active matrix displays, displays of the IPS (in plane switching) or VA (vertically aligned) mode like VAN (vertically aligned nematic) or VAC (vertically aligned cholesteric), displays of the ECB (electrically controlled birefringence), DAP (deformation of aligned phases), CSH (colour super homeotropic) or ASM (axially symmetric microcell) mode, phase-change, guest-host, flexoelectric, ferroelectric displays, bistable nematic and cholesteric displays like PSCT (polymer stabilized cholesteric texture), or PDLC, polymer gel or polymer network displays.

The compounds of formula I and polymerisable liquid crystal mixtures according to the present invention are epsecially suitable for the preparation of alignment layers or optical films having a pattern of regions with different orientation by photoalignment utilizing irradiation with linear polarized light, as described for example in U.S. Pat. No. 5,602,661, or for the preparation of cholesteric or multidomain liquid crystal displays, as disclosed in WO 98/57223.

Also, they are suitable for the preparation of polymer films with cholesteric structure having a pattern of at least two regions which differ in one or more properties selected from twist sense, reflection wavelength and birefringence, or for the preparation of cholesteric films having a broad reflection bandwidth, as described for example in EP 1 247 796, EP 1 247 797 and EP 1 295 929. Such films can be used for example as security markings or as optical films for LC displays (LCD), like colour filters or retarders, in particular for incell use in LCDs, i.e. for application inside the switchable LC cell of the display.

The compounds of formula I can further be used for the prepration of films comprising a pattern of regions or areas wih different orientation and/or retardation, as described for example in EP 03007017.2 or EP 03007918.0.

Thus, the invention further relates to an anisotropic polymer film as described above and below, which is obtained from one or more compounds of formula I or from a polymerisable LC material comprising one or more compounds of formula I, characterized in that the film has a pattern of at least two regions which differ in one or more properties selected from twist sense, reflection wavelength, birefringence and retardation.

An especially preferred embodiment of the present invention relates to a film comprising a polymerised liquid crystal (LC) material comprising at least one photoisomerisable compound, characterized in that it comprises at least two regions or areas with different retardation and/or at least two regions or areas with different orientation of the LC material, wherein said material comprises at least one compound of formula I. Especially preferred is a patterned film comprising at least two regions with different retardation and at least two regions with different orientation of the LC material.

Further preferred is a patterned retardation film, for example a patterned quarter wave film (QWF) or half wave film (HWF). Especially preferred is a film having a pattern of areas with a specific retardation, such as quarter or half wave retardation, and areas with no retardation, or a film having a pattern of areas with different values of the retardation.

The above films are preferably prepared by a process comprising the following steps, which is another object of the invention:

a) providing a layer of a polymerisable LC material comprising at least one photoisomerisable compound of formula I onto a substrate, b) aligning the layer of LC material into planar orientation, c) exposing the LC material in the layer, or in selected regions thereof, to photoradiation that causes isomerisation of the isomerisable compound, preferably UV radiation,
d) polymerising the LC material in at least a part of the exposed regions of the material, thereby fixing the orientation, and
e) optionally removing the polymerised film from the substrate, wherein the retardation and/or orientation of the LC material is controlled by varying the amount and/or type of the photoisomerisable compound, and/or by varying the dose of the photoradiation and/or the exposure time.

Further it is possible to prepare a multilayer comprising at least two layers of polymerised LC material having different orientation, by a process comprising the following steps, which is another object of the invention:
A) providing a first layer of a polymerisable LC material comprising at least one photoisomerisable compound of formula I onto a substrate,
B) aligning the first layer of LC material into planar orientation and polymerising the material, thereby fixing the orientation,
C) providing a second layer of LC material as described in steps A) and B), wherein the first layer serves as substrate, wherein the LC material in at least one of said first and second layers, or in selected regions thereof, before polymerisation is exposed to photoradiation that causes isomerisation of the isomerisable compound, preferably UV radiation.

The invention further relates to films or multilayers obtained by above methods.

The patterneds film are preferably prepared by a process comprising steps a) to e) as described above. The steps a) to e) can be carried out according to standard procedures that are known to the expert and are described in the literature, or according to the methods as described above. In the above process, the polymerisable LC material comprises a photoisomerisable compound, preferably a photoisomerisable mesogenic or LC compound, very preferably a photoisomerisable compound that is also polymerisable. The isomerisable compound changes its shape, e.g. by E-Z-isomerisation, when exposed to radiation of a specific wavelength, e.g. UV-radiation. This leads to disruption of the uniform planar orientation of the LC material, resulting in a drop of its birefringence.

Since the optical retardation of an oriented LC layer is given as the product $d \cdot \Delta n$ of the layer thickness d and the birefringence $\Delta n$ of the LC material, the drop in birefringence also causes a decrease of the retardation in the irradiated parts of the LC material. The orientation and retardation of the LC material is then fixed by in-situ polymerisation of the irradiated regions or of the entire film.

The degree of isomerisation and thus the birefringence change in the layer of LC material can be controlled e.g. by varying the radiation dose, intensity, time and/or power. Also, by applying a photomask between the radiation source and the LC layer it is possible to prepare a film with a pattern of regions or pixels having specific values of the retardation that differ from each other. For example, a film comprised of two different values of retardation can be created using a simple, monochrome mask. A more complicated film exhibiting multiple regions of different retardation can be created using a grey-scale mask. After the desired retardation values are achieved the LC layer is polymerised. In this way it is possible to create a polymer retardation film with values of retardation ranging from that of the initial LC layer to zero. The value of retardation for the initial layer of LC material is controlled by appropriate selection of the layer thickness and the type and amounts of the indivdual components of the LC material.

The polymerisable LC material for use in this preferred embodiment is preferably a nematic or smectic LC material, in particular a nematic material, and preferably comprises at least one di- or multireactive achiral RM and optionally one or more than one monoreactive achiral RMs. By using di- or multireactive RMs a crosslinked film is obtained, which exhibits high mechanical stability and high stability of the optical properties against external influences like temperature or solvents. Films comprising crosslinked LC material are thus especially preferred. The mono-, di- and multireactive RMs are preferably selected from the list comprising (R1) to (R23) as described above.

In a further preferred embodiment, the films according to the present invention are used as optical retardation film or colour filter in an LCD not outside the switchable LC cell of the display, but between the substrates, usually glass substrates, forming the switchable LC cell and containing the switchable LC medium (incell application).

Compared to conventional displays where optical retardation films are usually placed between the LC cell and the polarisers, incell application of an optical retardation film has several advantages. For example, a display where the optical film is attached outside of the glass substrates forming the LC cell usually suffers from parallax problems, which can severely impair viewing angle properties. If the retardation films is prepared inside the LC display cell, these parallax problems can be reduced or even avoided.

An LCD according to this embodiment preferably comprises
1) a liquid crystal (LC) cell comprising the following elements, starting from the edges to the centre of the cell in the sequence listed below
   11) a first and a second substrate plane parallel to each other, at least one of which is transparent to incident light,
   12) an array of nonlinear electric elements on one of said substrates which can be used to individually switch individual pixels of said LC cell, said elements being preferably active elements like transistors, very preferably TFTs,
   13) a colour filter array provided on one of said substrates, preferably on the substrate opposite to that carrying the array of nonlinear elements, said colour filter optionally being covered by a planarisation layer,
   14) a first electrode layer provided on the inside of said first substrate,
   15) optionally a second electrode layer provided on the inside of said second substrate,
   16) optionally first and second alignment layers provided on said first and second electrodes,
   17) an LC medium that is switchable between at least two different states by application of an electric field,
2) a first linear polariser on one side of the LC cell,
3) optionally a second linear polariser on the side of the LC cell opposite to that of the first linear polariser, and
4) at least one patterned optical retardation film according to the present invention, characterized in that said patterned optical retardation films 4) is situated between the first and second substrate of the LC cell, preferably between the colour filter and the liquid crystal medium, very preferably between the colour filter and one of said electrode layers, or if a planarisation layer is present, between the planarising layer and one of said electrode layers.

The polymerisable compounds and materials of the present invention are also suitable for the preparation of biaxial films having biaxial negative C-type symmetry, with principal refractive indices $n_x$ and $n_y$ in orthogonal directions in the film plane and $n_z$ perpendicular to the film plane, wherein $n_x \neq n_y \neq n_z$ and $n_x$, $n_y > n_z$, especially $n_x > n_y > n_z$.

For example, the compounds of formula I can be used for preparing optically biaxial films as described in EP04015969.1, which comprise an anisotropic material with helically twisted structure having a uniform helix and a local birefringence that varies periodically in the direction of the helical axis, preferably reflecting light of less than 400 nm (hereinafter also referred to as type 1). Furthermore, they can be used for the preparation of optically biaxial films as described in EP04015970.9, which comprise an anisotropic material with helically twisted structure having a deformed (or distorted) helix and a local birefringence that varies periodically in the direction of the helical axis (hereinafter also referred to as type 2).

For the preparation of type 1 biaxial films, preferably a cholesteric polymerisable LC material is used that comprises one or more compounds of formula I, one or more chiral compounds which induce the cholesteric structure, and a photoinitiator. Instead of using additional chiral compounds, one or more chiral compounds of formula I can be used. The polymerisable material is applied onto a substrate and aligned in planar orientation. The amount and helical twisting power (HTP) of the chiral compounds is preferably selected such that the cholesteric material has a short pitch and a reflection wavelength <400 nm. The material is then irradiated with linear polarised UV light that induces photoisomerisation of the compounds of formula I and a change of their refractive index. This leads to a change in birefringence locally within selected parts of the cholesteric helix. As the material is irradiated with polarised light, only those domains of the helix in which the LC director falls along the direction of polarised light will undergo photoreaction, thus reducing the birefringence only in those areas. At the same time the photoinitiator begins the polymerisation process which 'fixes' the helix structure whilst 'trapping' the photosensitive materials in their high or low birefringence state according to their position within the helix. In this way the helix structure remains uniform but the birefringence varies locally through the helix, leading to a biaxial optical film.

For the preparation of type 2 biaxial films, preferably a cholesteric polymerisable LC material is used as in type 1 above, but wherein the photoinitiator is a dichroic or LC photoinitiator for example as disclosed in EP-A-1388538. The material is again applied onto a substrate, aligned in planar orientation and irradiated with linear polarised UV light to provide a birefringence that varies locally through the helix. In addition, the dichroic photoinitiator locally aligns with its UV-absorbing axis parallel to the LC director. Upon polarised UV irradiation the LC photoiniator produces polymerisation-initiating free radicals predominantly where the local director lies parallel to the direction of polarisation. This results in local polymerisation, predominantly of di- or multifunctional polymerisable compounds, leading to a concentration gradient between high and low reactive components within a half turn of the helix. Highly reactive components become concentrated where the director lies parallel to the E-field (maximum concentration of free radicals) and the less reactive components, like monofunctional polymerisable or non-polymerisable compounds, become concentrated where the director is perpendicular to the E-field. Localised variation of the chiral component results in distortion of the sinusoidal helix, giving a 'distorted' or 'deformed' helix and an optically biaxial film.

Preferably, the biaxial films have a helical pitch reduced to values well below the visible wavelengths, so that only the average directional refractive indices are experienced. As a consequence the Bragg reflection bands occur in the UV, so the films are transparent to visible wavelengths of light and behave purely as retarders for these visible wavelengths.

In the foregoing and in the following examples, unless otherwise indicated, all temperatures are set forth uncorrected in degrees Celsius and all parts and percentages are by weight. The following abbreviations are used to illustrate the liquid crystalline phase behaviour of the compounds: K=crystalline; N=nematic; S=smectic; Ch=cholesteric; I=isotropic. The numbers between the symbols indicate the phase transition temperatures in ° C. Furthermore, mp. is the melting point, Δn is the optical anisotropy measured at 20° C. and 589 nm, Δε is the dielectric anisotropy at 20° C. and 1 kHz.

EXAMPLE 1

Compound (1) is prepared as follows

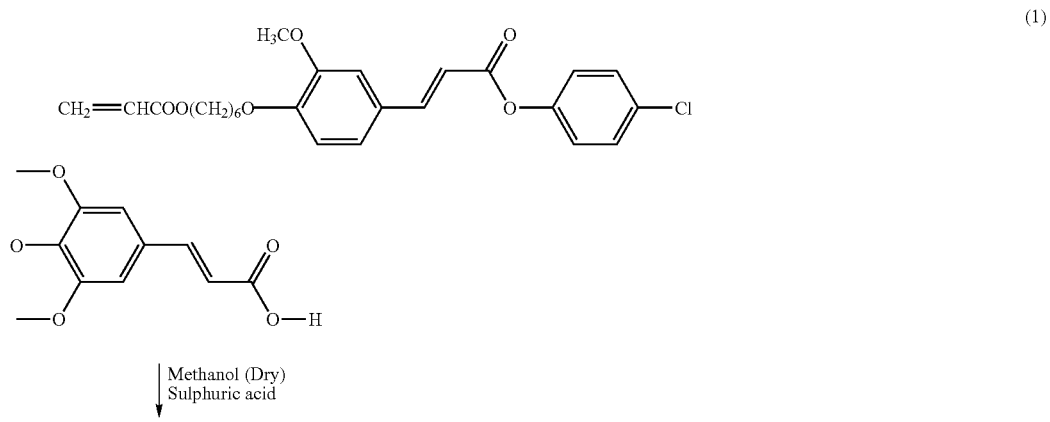

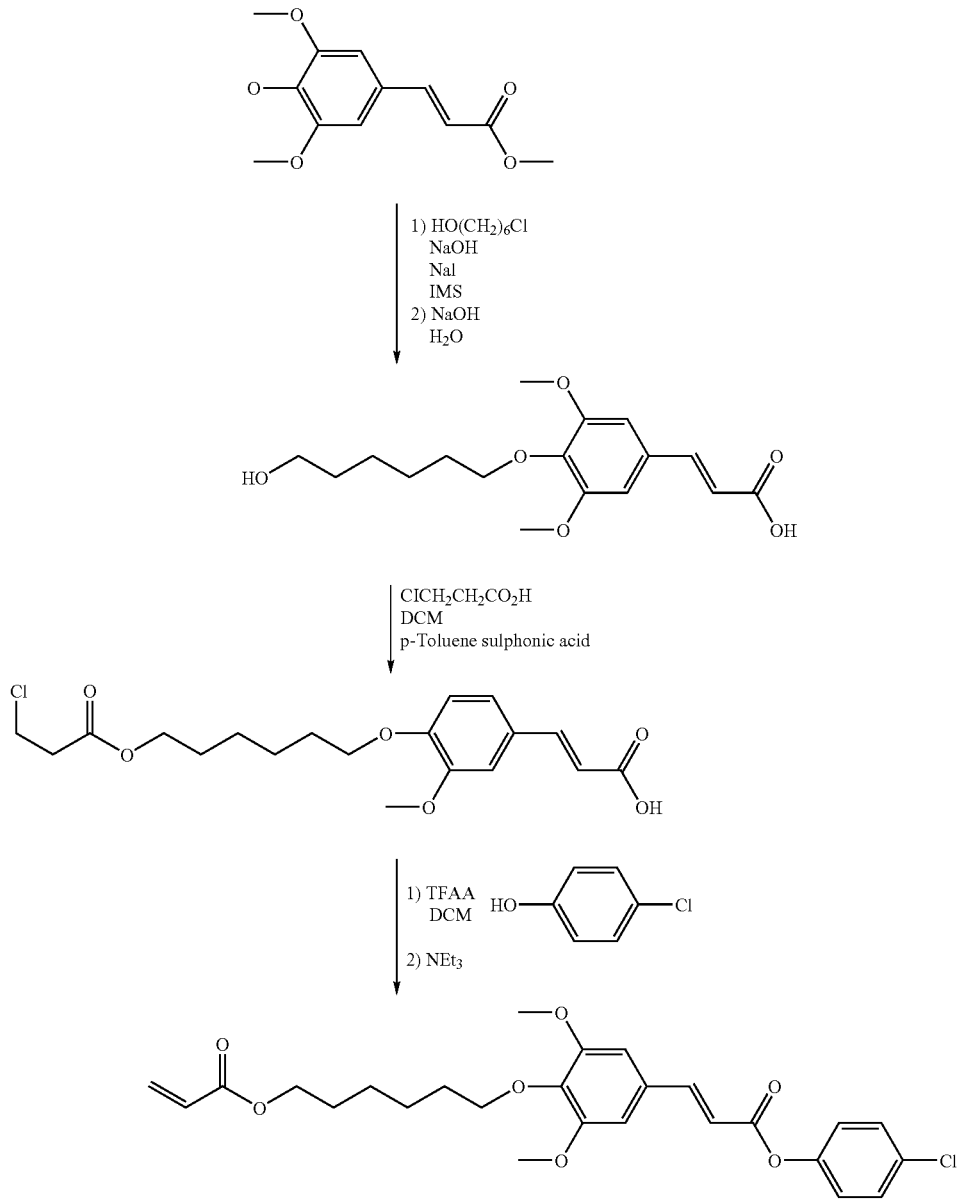

The following compound is prepared analoguously

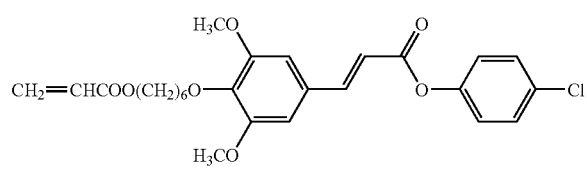

Compound (1) melts from a crystalline solid to liquid at 87.0° C.

Compound (2) melts from a crystalline solid to liquid at 69.7° C.

EXAMPLE 2

The compounds (1) and (2) of example 1 are used to create photoisomerisable retardation films. For comparison an analogous mixture containing a non-laterally substituted prior art cinnamate RM (3) is also prepared. In each case 15 mol % of the compound (1), (2) or (3), respectively, are added to a polymerisable nematic host mixture having the following composition

| | |
|---|---|
| (4) | 39.40% |
| (5) | 24.60% |
| (6) | 24.60% |
| (7) | 9.72% |
| Irgacure651 | 1.00% |

| | |
|---|---|
| Fluorad FC171 | 0.60% |
| Irganox1076 | 0.08% |

(4)
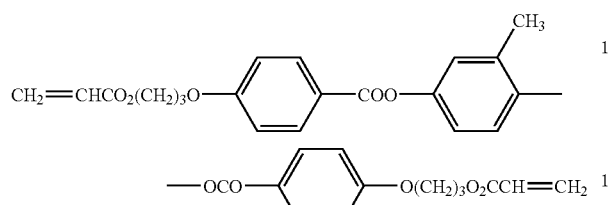

(5)
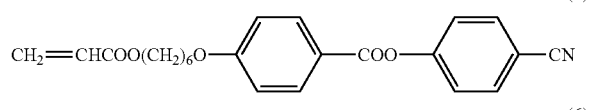

(6)
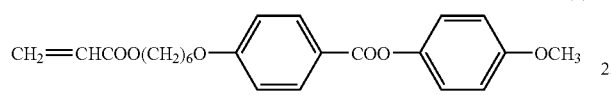

(7)
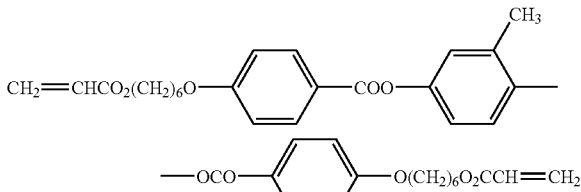

Irgacure651 ® is a photoinitiator, Irganox1076 ® a stabilizer, both being commercially available (Ciba AG, Basel, Switzerland). FC171 ® is a non-ionic fluorocarbon surfactant (from 3M Co.).

The solid mixtures are dissolved in PGMEA to create a 50% solution (by weight). The solutions are filtered (0.2 μm PTFE filter) and spincoated onto rubbed polyimide (JSR AL1054)/glass slides. Each slide is exposed to UV radiation in an air atmosphere (300s, 35 mWcm$^{-2}$, 365 nm, air) and subsequently photopolymerised (10s, 20 mWcm$^{-2}$, UV-A, $N_2$). For control experiments samples are spincoated and immediately photopolymerised (10s, 20 mWcm$^{-2}$, UV-A, $N_2$). The on-axis retardation of each film is measured. The extent of change in retardation is determined by comparing the isomerised and non-isomerised retardation values. The results are shown below.

| Mixture | Cinnamic RM in mixture | % retardation drop |
|---|---|---|
| 1 (prior art) | 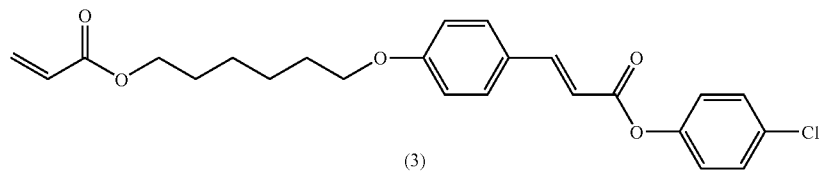 (3) | 8.8 |
| 2 | 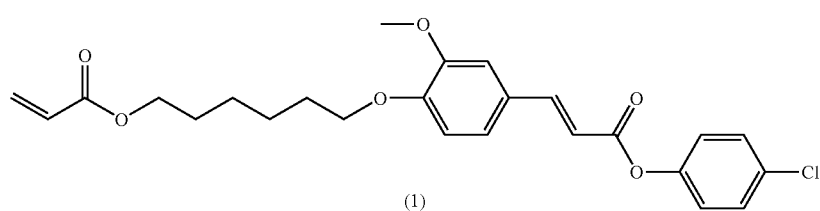 (1) | 15.7 |
| 3 | 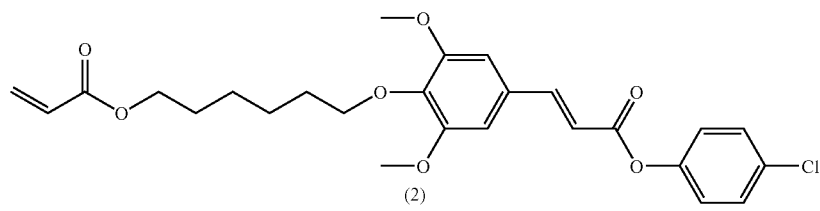 (2) | 15.5 |

The results show that, for a given mol % of cinnamate RM, the laterally substituted materials according to example 1 and 2 of the present invention provide a greater change in retardation. Therefore, as well as facilitating the synthesis, these materials also perform better in photoisomerisable mixtures.

The preceding examples can be repeated with similar success by substituting the generically or specifically described reactants and/or operating conditions of this invention for those used in the preceding examples.

The entire disclosures of all applications, patents and publications, cited herein and of corresponding European application No. 03023430.6, filed Oct. 17, 2003 are incorporated by reference herein.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A compound of formula I

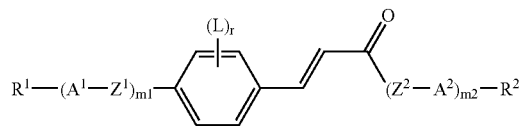

wherein
$A^1$ and $A^2$ are, each independently, an aliphatic or aromatic carbocyclic or heterocyclic group with up to 20 C atoms that may comprise fused rings and may be unsubstituted, mono- or polysubstituted with L,
m1 is 0, 1, 2 or 3,
m2 is 1, 2, 3 or 4,
$Z^1$ to $Z^2$ are, independently of each other, —O—, —S—, —CO—, —COO—, —OCO—, —S—CO—, —CO—S—, —O—COO—, —CO—NR$^0$—, —NR$^0$—CO—, —OCH$_2$—, —CH$_2$O—, —SCH$_2$—, —CH$_2$S—, —CF$_2$O—, —OCF$_2$—, —CF$_2$S—, —SCF$_2$—, —CH$_2$CH$_2$—, —CF$_2$CH$_2$—, —CH$_2$CF$_2$—, —CF$_2$CF$_2$—, —CH=N—, —N=CH—, —N=N—, —CH=CR$^0$—, —CY$^1$=CY$^2$—, —C≡C—, —CH=CH—COO—, —OCO—CH=CH— or a single bond,
$Y^1$ and $Y^2$ are, independently of each other, H, F, Cl or CN,
$R^0$ and $R^{00}$ are, independently of each other, H or alkyl with 1 to 12 C-atoms,
$R^1$ and $R^2$ are, independently of each other, H, F, Cl, Br, I, CN, NO$_2$, NCS, SF$_5$ or a straight chain or branched alkyl having 1 to 30 C-atoms that is unsubstituted, mono- or poly-substituted by F, Cl, Br, I or CN, and in which one or more non-adjacent CH$_2$ groups are optionally replaced, in each case independently from one another, by —O—, —S—, —NH—, —NR$^0$—, —SiR$^0$R$^{00}$—, —CO—, —COO—, —OCO—, —OCO—O—, —S—CO—, —CO—S—, —CY$^1$=CY$^2$— or —C≡C— in such a manner that O and/or S atoms are not linked directly to one another, or denote P-Sp, wherein at least one of $R^1$ and $R^2$ is P-Sp,
P is a polymerizable group,
Sp is a spacer group or a single bond,
L has, in case of multiple occurrence independently of one another, one of the meanings of $R^1$ different from H, and
r is 1, 2, 3 or 4.

2. A compound according to claim 1, wherein $R^1$ or $R^2$ is F, Cl, CN or an alkyl, alkoxy, sulfanylalkyl, thiocarboxyl, alkylsulfonyl or alkenyl with 1 to 12 C-atoms, any of which is optionally fluorinated.

3. A compound according to claim 1, wherein m1 is 0 and m2 is 1 or 2.

4. A compound according to claim 1, wherein $R^1$ is P-Sp.

5. A compound of formula I

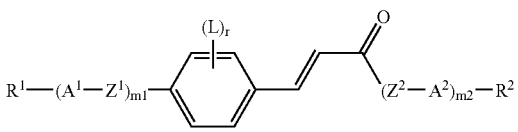

wherein
$A^1$ and $A^2$ are, each independently, furane-2,5-diyl, thiophene-2,5-diyl, pyrrol-2,5-diyl, 1,4-phenylene, pyridine-2,5-diyl, pyrimidine-2,5-diyl, naphthalene-2,6-diyl, 1,2,3,4-tetrahydro-naphthalene-2,6-diyl, indane-2,5-diyl, or 1,4-cyclohexylene, in any of which one or two non-adjacent CH$_2$ groups may be replaced by O and/or S, any of which is unsubstituted or mono- or polysubstituted by L,
m1 is 0, 1, 2 or 3,
m2 is 1, 2, 3 or 4,
$Z^1$ to $Z^2$ are independently of each other —O—, —S—, —CO—, —COO—, —OCO—, —S—CO—, —CO—S—, —O—COO—, —CO—NR$^0$—, —NR$^0$—CO—, —OCH$_2$—, —CH$_2$O—, —SCH$_2$—, —CH$_2$S—, —CF$_2$O—, —OCF$_2$—, —CF$_2$S—, —SCF$_2$—, —CH$_2$CH$_2$—, —CF$_2$CH$_2$—, —CH$_2$CF$_2$—, —CF$_2$CF$_2$—, —CH=N—, —N=CH—, —N=N—, —CH=CR$^0$—, —CY$^1$=CY$^2$—, —C≡C—, —CH=CH—COO—, —OCO—CH=CH— or a single bond,
$Y^1$ and $Y^2$ are independently of each other H, F, Cl or CN,
$R^0$ and $R^{00}$ are independently of each other H or alkyl with 1 to 12 C-atoms,
$R^1$ and $R^2$ are independently of each other H, F, Cl, Br, I, CN, NO$_2$, NCS, SF$_5$ or a straight chain or branched alkyl having 1 to 30 C-atoms that is unsubstituted, mono- or poly-substituted by F, Cl, Br, I or CN, and in which one or more non-adjacent CH$_2$ groups are optionally replaced, in each case independently from one another, by —O—, —S—, —NH—, —NR$^0$—, —SiR$^0$R$^{00}$—, —CO—, —COO—, —OCO—, —OCO—O—, —S—CO—, —CO—S—, —CY$^1$=CY$^2$— or —C≡C— in such a manner that O and/or S atoms are not linked directly to one another, or denote P-Sp, wherein at least one of $R^1$ and $R^2$ is P-Sp,
P is a polymerizable group,
Sp is a spacer group or a single bond,
L has, in case of multiple occurrence independently of one another, one of the meanings of $R^1$ different from H, and
r is 1, 2, 3 or 4.

6. A compound according to claim 1, wherein

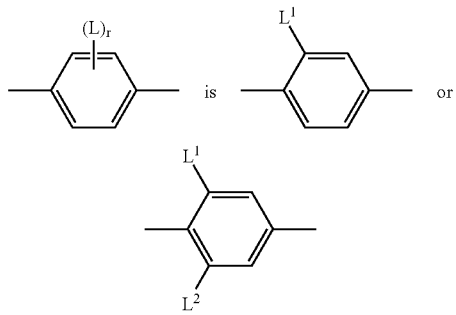

wherein $L^1$ and $L^2$ have independently of each other one of the meanings of L in formula I.

7. A compound of formula I1

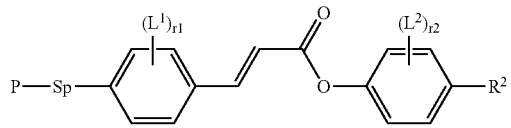

wherein

P is a polymerizable group,

Sp is a spacer group or a single bond, $R^2$ is H, F, Cl, Br, I, CN, $NO_2$, NCS, $SF_5$ or a straight chain or branched alkyl having 1 to 30 C-atoms that is unsubstituted, mono- or poly-substituted by F, Cl, Br, I or CN, and in which one or more non-adjacent $CH_2$ groups are optionally replaced, in each case independently from one another, by —O—, —S—, —NH—, —$NR^o$—, —$SiR^oR^{oo}$—, —CO—, —COO—, —OCO—, —OCO—O—, —S—CO—, —CO—S—, —$CY^1$=$CY^2$— or —C≡C— in such a manner that O and/or S atoms are not linked directl to one another or denote P-Sp, $L^1$ and $L^2$ are, independently of each other, H, F, Cl, Br, I, CN, $NO_2$, NCS, $SF_5$ or a straight chain or branched alkyl having 1 to 30 C-atoms that is unsubstituted, mono- or poly-substituted b F, Cl, Br, I or CN, and in which one or more non-adjacent $CH_2$ groups are optionally replaced, in each case independently from one another, by —O—, —S—, —NH—, —$NH^o$—, —$SiR^oR^{oo}$—, —CO—, —COO—, —OCO—, —OCO—O—, —S—CO—, —CO—S—, —$CY^1$=$CY^2$— or —C≡C— in such a manner that O and/or S atoms are not linked directly to one another, or denote P-Sp, r1 is 1, 2, 3 or 4, and r2 is 0, 1, 2, 3 or 4.

8. A compound according to claim 7, which is of formula I1a, I1b, I1c, or I1d

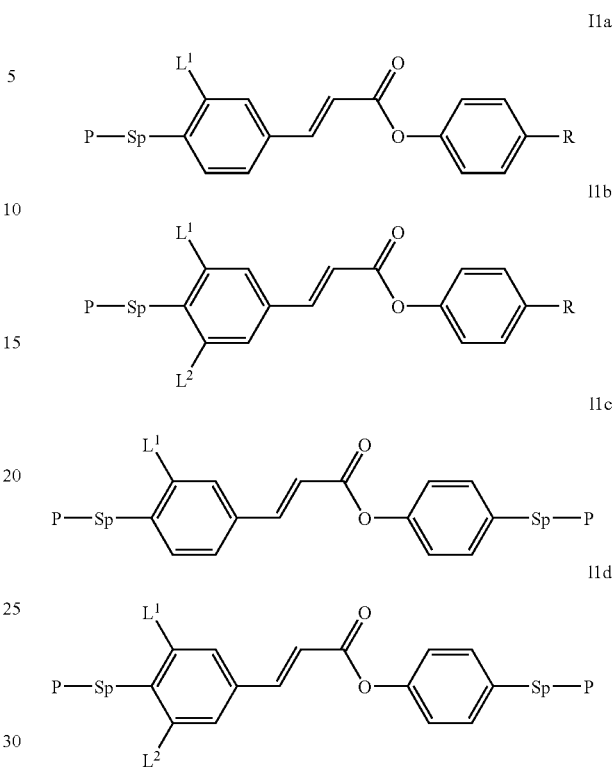

wherein

R is H, F, Cl, Br, I, CN, $NO_2$, NCS, $SF_5$ or a straight chain or branched alkyl having 1 to 30 C-atoms that is unsubstituted, mono- or poly-substituted by F, Cl, Br, I or CN, and in which one or more non-adjacent $CH_2$ groups are optionally replaced, in each case independently from one another, by —O—, —S—, —NH—, —$NR^o$—, —$SiR^oR^{oo}$—, —CO—, —COO—, —OCO—, —OCO—O—, —S—CO—, —CO—S—, —$CY^1$=$CY^2$— or —C≡C— in such a manner that O and/or S atoms are not linked directl to one another, P is a polymerizable group, Sp is a spacer group or a single bond, and $L^1$ and $L^2$ are, independently of each other, H, F, Cl, Br, I, CN, $NO_2$, NCS, $SF_5$ or a straight chain or branched alkyl having 1 to 30 C-atoms that is unsubstituted, mono- or poly-substituted by F, Cl, Br, I or CN, and in which one or more non-adjacent $CH_2$ groups are optionally replaced, in each case independently from one another, by —O—, —S—, —NH—, —$NR^o$—, —$SiR^oR^{oo}$—, —CO—, —COO—, —OCO—, —OCO—O—, —S—CO—, —CO—S—, —$CY^1$=$CY^2$— or —C≡C— in such a manner that O and/or S atoms are not linked directl to one another or denote P-Sp.

9. A polymerisable liquid crystal material comprising at least one compound according to claim 1.

10. An anisotropic polymer or polymer film obtained from a polymerisable liquid crystal material according to claim 9.

11. An anisotropic polymer film according to claim 10, which has a pattern of at least two areas which differ in one or more properties selected from twist sense, reflection wavelength, birefringence and retardation.

12. An anisotropic polymer film according to claim 11, which has a pattern of at least two areas having different retardation.

13. An anisotropic polymer film according to claim 12, which is a patterned quarter wave film.

14. An anisotropic polymer film according to claim 13, which is a patterned half wave film.

15. An anisotropic polymer film according to claim 10, which is an optically biaxial film.

16. An optical film, polariser, compensator, biaxial film, beam splitter, reflective film, alignment layer, colour filter, holographic element, hot stamping foil, coloured image, decorative or security marking, liquid crystal pigment, adhesive, synthetic resin with anisotropic mechanical properties, a cosmetic, a diagnostic product, a nonlinear optic device, optical information storage device, an electronic device, a field effect transistor (FET) as components of integrated circuitry, a thin film transistor in flat panel display application, or a Radio Frequency Identification (RFID) tag, a semiconducting component for organic light emitting diode (OLED) application, an electroluminescent display, a backlight of a liquid crystal display, a photovoltaic or sensor device, an electrode material in a battery, a photoconductor, an electrophotographic recording, comprising a compound according to claim 1.

17. An optical film, polariser, compensator, biaxial film, beam splitter, reflective film, alignment layer, colour filter, holographic element, hot stamping foil, coloured image, decorative or security marking, liquid crystal pigment, adhesive, synthetic resin with anisotropic mechanical properties, a cosmetic, a diagnostic product, a nonlinear optic device, optical information storage device, an electronic device, a field effect transistor (FET) as components of integrated circuitry, a thin film transistor in flat panel display application, or a Radio Frequency Identification (RFID) tag, a semiconducting component for organic light emitting diode (OLED) application, an electroluminescent display, a backlight of a liquid crystal display, a photovoltaic or sensor device, an electrode material in a battery, a photoconductor, an electrophotographic recording, comprising a polymerisable liquid crystal material acording to claim 9.

18. An optical film, polariser, compensator, biaxial film, beam splitter, reflective film, alignment layer, colour filter, holographic element, hot stamping foil, coloured image, decorative or security marking, liquid crystal pigment, adhesive, synthetic resin with anisotropic mechanical properties, a cosmetic, a diagnostic product, a nonlinear optic device, optical information storage device, an electronic device, a field effect transistor (FET) as components of integrated circuitry, a thin film transistor in flat panel display application, or a Radio Frequency Identification (RFID) tag, a semiconducting component for organic light emitting diode (OLED) application, an electroluminescent display, a backlight of a liquid crystal display, a photovoltaic or sensor device, an electrode material in a battery, a photoconductor, an electrophotographic recording, comprising an anisotropic polymer or polymer film according to claim 10.

19. An anisotropic polymer or polymer film obtained from a polymerisable liquid crystal material comprising at least one compound according to claim 7.

20. An anisotropic polymer or polymer film obtained from a polymerisable liquid crystal material comprising at least one compound according to claim 8.

\* \* \* \* \*

UNITED STATES PATENT AND TRADEMARK OFFICE
CERTIFICATE OF CORRECTION

PATENT NO. : 7,294,369 B2 Page 1 of 1
APPLICATION NO. : 10/965851
DATED : November 13, 2007
INVENTOR(S) : Richard Harding It is certified that error appears in the above-identified patent and that said Letters Patent is hereby corrected as shown below:

Column 33, line 40, reads "$Z^1$ to $Z^2$," should read -- $Z^1$ and $Z^2$, --
Column 34, line 36, reads "$Z^1$ to $Z^2$," should read -- $Z^1$ and $Z^2$, --
Column 34, line 46, reads "are independently of each other H," should read -- are, independently of each other, H, --
Column 34, line 47, reads "are independently of each other H," should read -- are, independently of each other, H, --
Column 34, line 49, reads "are independently of each other H," should read -- are, independently of each other, H, --
Column 35, line 18, reads "having independently of each other one" should read -- have, independently of each other, one --
Column 35, line 46, reads "linked directl to" should read -- linked directly to --
Column 35, line 52, poly-substituted b F," should read -- poly-substituted by F, --
Column 35, line 56, reads "-$NH^°$-," should read -- -$NR^°$-, --
Column 36, line 44, reads "linked directl to" should read -- linked directly to --
Column 36, line 59, reads "linked directl to" should read -- linked directly to --

Signed and Sealed this

Twentieth Day of May, 2008

JON W. DUDAS
*Director of the United States Patent and Trademark Office*